US009874556B2

(12) United States Patent
O'Farrell et al.

(10) Patent No.: US 9,874,556 B2
(45) Date of Patent: *Jan. 23, 2018

(54) LATERAL FLOW ASSAYS USING TWO DIMENSIONAL FEATURES

(71) Applicant: Symbolics, LLC, Irvine, CA (US)

(72) Inventors: Brendan O'Farrell, Santa Ana, CA (US); Thomas C. Tisone, Orange, CA (US)

(73) Assignee: Symbolics, LLC, Irvine, CA (US)

( * ) Notice: Subject to any disclaimer, the term of this patent is extended or adjusted under 35 U.S.C. 154(b) by 1185 days.

This patent is subject to a terminal disclaimer.

(21) Appl. No.: 13/802,036

(22) Filed: Mar. 13, 2013

(65) Prior Publication Data

US 2014/0024016 A1    Jan. 23, 2014

Related U.S. Application Data

(60) Provisional application No. 61/673,156, filed on Jul. 18, 2012.

(51) Int. Cl.
*G01N 33/558* (2006.01)
*G01N 33/543* (2006.01)
*B01L 3/00* (2006.01)

(52) U.S. Cl.
CPC ...... *G01N 33/54386* (2013.01); *B01L 3/5023* (2013.01); *G01N 33/558* (2013.01); *B01L 2200/148* (2013.01); *B01L 2300/028* (2013.01)

(58) Field of Classification Search
None
See application file for complete search history.

(56) References Cited

U.S. PATENT DOCUMENTS

| 3,641,235 A | 2/1972 | Weiss |
| 3,959,078 A | 5/1976 | Guire |
| 3,966,897 A | 6/1976 | Renn et al. |
| 4,094,647 A | 6/1978 | Deutsch et al. |
| 4,168,146 A | 9/1979 | Grubb et al. |
| 4,299,916 A | 11/1981 | Litman et al. |
| 4,332,788 A | 6/1982 | Mochida et al. |

(Continued)

FOREIGN PATENT DOCUMENTS

| CA | 2 216 214 | 5/1999 |
| CN | 1800831 | 7/2006 |

(Continued)

OTHER PUBLICATIONS

International Preliminary Report on Patentability in PCT/US2013/050952, mailed Aug. 28, 2014, 10 pages.

(Continued)

*Primary Examiner* — Chris L Chin
(74) *Attorney, Agent, or Firm* — Morrison & Foerster LLP

(57) ABSTRACT

The present invention relates to novel lateral flow devices using two dimensional features, preferably, uniform two dimensional test and control features, to provide flow control information, to function as an internal control and/or to provide internal calibration information for the test device. The present invention also relates to methods for using the lateral flow devices to provide flow control information, to function as an internal control and/or to provide internal calibration information for the test device.

22 Claims, 4 Drawing Sheets

(56) References Cited

U.S. PATENT DOCUMENTS

Figure 1A:
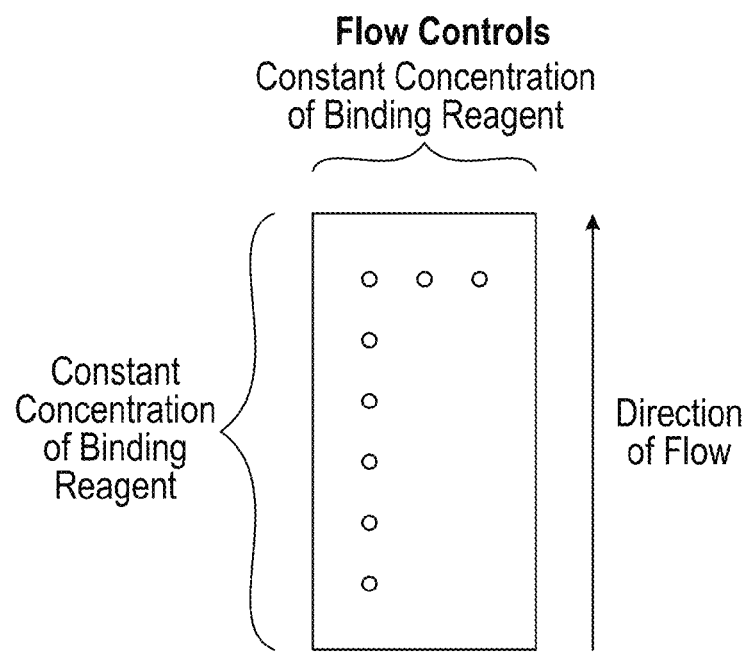

| Patent | Date | Inventor |
|---|---|---|
| 4,347,312 A | 8/1982 | Brown et al. |
| 4,366,241 A | 12/1982 | Tom et al. |
| 4,373,932 A | 2/1983 | Gribnau et al. |
| 4,391,904 A | 7/1983 | Litman et al. |
| 4,425,438 A | 1/1984 | Bauman et al. |
| 4,517,288 A | 5/1985 | Giegel et al. |
| 4,695,554 A | 9/1987 | O'Connell et al. |
| 4,703,017 A | 10/1987 | Campbell et al. |
| 4,740,468 A * | 4/1988 | Weng .......... G01N 33/538 435/7.91 |
| 4,743,560 A | 5/1988 | Campbell et al. |
| 4,778,751 A * | 10/1988 | El Shami .......... G01N 33/531 435/7.5 |
| 4,857,453 A | 8/1989 | Ullman et al. |
| 4,861,711 A | 8/1989 | Friesen et al. |
| 4,956,302 A | 9/1990 | Gordon et al. |
| 4,960,691 A | 10/1990 | Gordon et al. |
| 5,073,484 A | 12/1991 | Swanson et al. |
| 5,075,078 A | 12/1991 | Osikoqicz |
| 5,079,142 A | 1/1992 | Coleman et al. |
| 5,120,643 A | 6/1992 | Ching et al. |
| 5,132,085 A | 7/1992 | Pelanek |
| 5,141,875 A | 8/1992 | Kelton et al. |
| 5,160,701 A * | 11/1992 | Brown, III .......... G01N 33/521 422/408 |
| 5,236,826 A | 8/1993 | Marshall |
| 5,252,459 A | 10/1993 | Tarcha et al. |
| 5,252,496 A | 10/1993 | Kang et al. |
| 5,275,785 A | 1/1994 | May et al. |
| 5,378,638 A | 1/1995 | Deeg et al. |
| 5,401,667 A | 3/1995 | Koike |
| 5,422,726 A | 6/1995 | Tyler |
| 5,501,949 A | 3/1996 | Marshall |
| 5,504,013 A | 4/1996 | Senior |
| 5,514,602 A | 5/1996 | Brooks, Jr. et al. |
| 5,559,041 A | 9/1996 | Kang et al. |
| 5,571,726 A | 11/1996 | Brooks, Jr. et al. |
| 5,578,577 A | 11/1996 | Ching et al. |
| 5,591,645 A | 1/1997 | Rosenstein |
| 5,596,414 A | 1/1997 | Tyler |
| 5,602,040 A | 2/1997 | May et al. |
| 5,622,871 A | 4/1997 | May et al. |
| 5,654,162 A | 8/1997 | Guire et al. |
| 5,656,448 A | 8/1997 | Kang et al. |
| 5,656,503 A | 8/1997 | May et al. |
| 5,710,005 A | 1/1998 | Rittenburg |
| 5,712,170 A | 1/1998 | Kouvonen et al. |
| 5,714,389 A | 2/1998 | Charlton et al. |
| 5,716,778 A | 2/1998 | Weng et al. |
| 5,728,587 A | 3/1998 | Kang et al. |
| 5,747,273 A | 5/1998 | Khosravi et al. |
| 5,753,517 A | 5/1998 | Brooks et al. |
| 5,798,273 A | 8/1998 | Shuler et al. |
| 5,837,546 A | 11/1998 | Allen et al. |
| 5,869,252 A | 2/1999 | Bouma et al. |
| 5,915,386 A | 6/1999 | Lloyd et al. |
| 5,965,458 A | 10/1999 | Kouvonen et al. |
| 5,968,839 A | 10/1999 | Blatt et al. |
| 5,989,921 A | 11/1999 | Charlton et al. |
| 6,017,767 A | 1/2000 | Chandler |
| 6,020,147 A | 2/2000 | Guire et al. |
| 6,027,943 A | 2/2000 | Kang et al. |
| 6,077,222 A | 6/2000 | Lloyd et al. |
| 6,080,106 A | 6/2000 | Lloyd et al. |
| 6,100,099 A | 8/2000 | Gordon et al. |
| 6,103,536 A | 8/2000 | Geisberg |
| 6,121,008 A | 9/2000 | Fitzpatrick et al. |
| 6,140,048 A | 10/2000 | Muller et al. |
| 6,140,134 A | 10/2000 | Rittenburg |
| 6,156,271 A | 12/2000 | May |
| 6,186,962 B1 | 2/2001 | Lloyd et al. |
| 6,187,269 B1 | 2/2001 | Lancesseur et al. |
| 6,187,598 B1 | 2/2001 | May et al. |
| 6,194,222 B1 | 2/2001 | Buechler et al. |
| 6,210,898 B1 | 4/2001 | Bouma et al. |
| D441,298 S | 5/2001 | Gundlach et al. |
| 6,228,660 B1 | 5/2001 | May et al. |
| 6,241,862 B1 | 6/2001 | McAleer et al. |
| 6,267,722 B1 | 7/2001 | Anderson et al. |
| 6,287,875 B1 | 9/2001 | Geisberg |
| 6,319,665 B1 | 11/2001 | Zwanziger et al. |
| 6,319,676 B1 | 11/2001 | Nazareth et al. |
| 6,352,862 B1 | 3/2002 | Davis et al. |
| 6,368,875 B1 | 4/2002 | Geisberg |
| 6,379,620 B1 | 4/2002 | Tydings et al. |
| 6,394,952 B1 | 5/2002 | Anderson et al. |
| 6,399,398 B1 | 6/2002 | Cunningham et al. |
| 6,403,380 B1 | 6/2002 | Catt et al. |
| 6,406,920 B1 | 6/2002 | Davis et al. |
| 6,409,662 B1 | 6/2002 | Lloyd et al. |
| 6,451,619 B1 | 9/2002 | Catt et al. |
| 6,454,726 B1 | 9/2002 | Catt et al. |
| 6,485,982 B1 | 11/2002 | Charlton |
| 6,506,612 B2 | 1/2003 | Kang et al. |
| 6,534,320 B2 | 3/2003 | Ching et al. |
| 6,541,277 B1 | 4/2003 | Kang et al. |
| 6,544,797 B1 | 4/2003 | Buechler et al. |
| 6,551,495 B1 | 4/2003 | Porter et al. |
| 6,585,663 B1 | 7/2003 | Coley et al. |
| 6,649,418 B1 | 11/2003 | Geisberg |
| D484,600 S | 12/2003 | Kaar et al. |
| RE38,430 E | 2/2004 | Rosenstein |
| 6,706,049 B2 | 3/2004 | Moerman |
| 6,707,554 B1 | 3/2004 | Miltner et al. |
| 6,719,923 B2 | 4/2004 | Stiene et al. |
| 6,737,277 B1 | 5/2004 | Kang et al. |
| 6,759,202 B2 | 7/2004 | Grossman et al. |
| 6,764,827 B1 | 7/2004 | Aoki et al. |
| 6,766,817 B2 | 7/2004 | da Silva |
| 6,767,709 B1 | 7/2004 | Suzuki et al. |
| 6,770,487 B2 | 8/2004 | Crosby |
| 6,777,198 B2 | 8/2004 | Mendel-Hartvig et al. |
| D497,673 S | 10/2004 | Long |
| 6,805,837 B2 | 10/2004 | Tydings |
| 6,805,838 B2 | 10/2004 | Tydings |
| D497,999 S | 11/2004 | Long |
| 6,812,038 B1 | 11/2004 | Mendel-Hartvig et al. |
| 6,818,455 B2 | 11/2004 | May et al. |
| 6,830,731 B1 | 12/2004 | Buechler et al. |
| 6,849,450 B2 | 2/2005 | Langley et al. |
| 6,861,214 B1 | 3/2005 | Rampal et al. |
| 6,867,051 B1 | 3/2005 | Anderson et al. |
| 6,916,666 B1 | 7/2005 | Mendel-Hartvig et al. |
| 6,927,064 B1 | 8/2005 | Catt et al. |
| 6,936,476 B1 | 8/2005 | Anderson et al. |
| D509,901 S | 9/2005 | Phelan et al. |
| D510,711 S | 10/2005 | Syme et al. |
| 6,951,631 B1 | 10/2005 | Catt et al. |
| 7,049,150 B2 | 5/2006 | Bachand |
| D523,964 S | 6/2006 | Phelan et al. |
| 7,081,348 B2 | 7/2006 | Suzuki et al. |
| 7,096,877 B2 | 8/2006 | Larsen et al. |
| 7,109,042 B2 | 9/2006 | May et al. |
| D530,825 S | 10/2006 | Lee et al. |
| D531,735 S | 11/2006 | Lee et al. |
| 7,138,269 B2 | 11/2006 | Blankenstein |
| 7,141,212 B2 | 11/2006 | Catt et al. |
| 7,153,651 B1 | 12/2006 | Drewes et al. |
| 7,153,681 B1 | 12/2006 | Penfold et al. |
| D536,798 S | 2/2007 | Lee et al. |
| 7,175,992 B2 | 2/2007 | Fong |
| 7,178,416 B2 | 2/2007 | Whelan et al. |
| 7,205,553 B2 | 4/2007 | Dorsel et al. |
| RE39,664 E | 5/2007 | Gordon et al. |
| 7,226,752 B1 | 6/2007 | Roitman |
| 7,238,537 B2 | 7/2007 | Davis et al. |
| 7,238,538 B2 | 7/2007 | Freitag et al. |
| 7,239,394 B2 | 7/2007 | Sharrock et al. |
| 7,244,392 B1 | 7/2007 | Konecke |
| 7,247,500 B2 | 7/2007 | Wei et al. |
| 7,256,053 B2 | 8/2007 | Hu |
| 7,270,970 B2 | 9/2007 | Anderson et al. |
| 7,280,201 B2 | 10/2007 | Helbing |
| 7,297,502 B2 | 11/2007 | Gao |

(56) References Cited

U.S. PATENT DOCUMENTS

| | | |
|---|---|---|
| D557,815 S | 12/2007 | Lee et al. |
| 7,305,896 B2 | 12/2007 | Howell et al. |
| 7,312,027 B2 | 12/2007 | Bachand |
| 7,315,378 B2 | 1/2008 | Phelan et al. |
| 7,317,532 B2 | 1/2008 | Sharrock et al. |
| 7,323,139 B2 | 1/2008 | LaBorde et al. |
| 7,371,582 B2 | 5/2008 | Nahm et al. |
| D570,490 S | 6/2008 | Laverack |
| D571,019 S | 6/2008 | Laverack |
| D571,020 S | 6/2008 | Laverack |
| 7,384,796 B2 | 6/2008 | Davis et al. |
| 7,391,512 B2 | 6/2008 | Fouquet et al. |
| D574,966 S | 8/2008 | Laverack |
| D575,876 S | 8/2008 | Laverack |
| D575,877 S | 8/2008 | Laverack |
| 7,407,813 B2 | 8/2008 | Davis et al. |
| 7,410,768 B2 | 8/2008 | Butlin et al. |
| 7,416,700 B2 | 8/2008 | Buechler et al. |
| D576,737 S | 9/2008 | Lee |
| 7,437,913 B2 | 10/2008 | Djennati et al. |
| 7,438,852 B2 | 10/2008 | Tung et al. |
| 7,459,314 B2 | 12/2008 | Guo et al. |
| 7,459,317 B2 | 12/2008 | Roitman |
| 7,476,549 B2 | 1/2009 | Nahm et al. |
| 7,510,881 B2 | 3/2009 | Ramael et al. |
| 7,516,845 B2 | 4/2009 | Lang et al. |
| 7,517,495 B2 | 4/2009 | Wu et al. |
| 7,521,259 B2 | 4/2009 | Petruno et al. |
| 7,521,260 B2 | 4/2009 | Petruno et al. |
| 7,522,762 B2 | 4/2009 | Rea et al. |
| 7,526,485 B2 | 4/2009 | Hagan et al. |
| D592,759 S | 5/2009 | Laverack |
| 7,532,128 B2 | 5/2009 | Petrilla |
| 7,534,393 B2 | 5/2009 | Catt et al. |
| 7,553,630 B2 | 6/2009 | Langley et al. |
| D597,216 S | 7/2009 | McGuigan et al. |
| 7,588,908 B2 | 9/2009 | Buechler et al. |
| 7,591,791 B2 | 9/2009 | Keren |
| D602,599 S | 10/2009 | Xiaowei |
| 7,616,315 B2 | 11/2009 | Sharrock et al. |
| 7,625,763 B2 | 12/2009 | Panotopoulos |
| 7,629,178 B2 | 12/2009 | Davis et al. |
| 7,632,460 B2 | 12/2009 | Catt et al. |
| 7,633,620 B2 | 12/2009 | Nahm et al. |
| 7,662,643 B2 | 2/2010 | Wei et al. |
| 7,679,745 B2 | 3/2010 | Claps et al. |
| 7,691,595 B2 | 4/2010 | Fong |
| 7,704,702 B2 | 4/2010 | Keren et al. |
| 7,704,753 B2 | 4/2010 | Tang et al. |
| 7,705,976 B2 | 4/2010 | Robrish |
| 7,713,703 B1 | 5/2010 | Buechler et al. |
| 7,718,443 B2 | 5/2010 | Beesley et al. |
| D617,468 S | 6/2010 | Marquordt et al. |
| 7,741,103 B2 | 6/2010 | Guirguis |
| 7,745,228 B2 | 6/2010 | Schwind et al. |
| 7,763,454 B2 | 7/2010 | Nazareth et al. |
| 7,763,475 B2 | 7/2010 | Klenerman et al. |
| D621,059 S | 8/2010 | Marquordt et al. |
| 7,775,976 B2 | 8/2010 | Fuller et al. |
| 7,784,678 B2 | 8/2010 | Kuo et al. |
| 7,785,899 B2 | 8/2010 | Saul et al. |
| 7,796,266 B2 | 9/2010 | Cohen et al. |
| 7,799,554 B2 | 9/2010 | Mazumdar et al. |
| 7,803,636 B2 | 9/2010 | Gao et al. |
| 7,815,853 B2 | 10/2010 | Nahm et al. |
| 7,815,854 B2 | 10/2010 | Cohen |
| 7,819,822 B2 | 10/2010 | Calasso et al. |
| 7,838,258 B2 | 11/2010 | Yang et al. |
| 7,842,472 B2 | 11/2010 | Valkirs et al. |
| 7,858,396 B2 | 12/2010 | Corstjens et al. |
| 7,863,268 B2 | 1/2011 | Makarov et al. |
| 7,873,939 B2 | 1/2011 | Tian et al. |
| 7,879,624 B2 | 2/2011 | Sharrock |
| 7,879,979 B2 | 2/2011 | Buechler et al. |
| D634,023 S | 3/2011 | Wei |
| D634,620 S | 3/2011 | Edwards |
| D634,621 S | 3/2011 | Edwards |
| 7,901,949 B2 | 3/2011 | Raj |
| 7,925,445 B2 | 4/2011 | Petrilla et al. |
| 7,939,342 B2 | 5/2011 | Song et al. |
| D639,976 S | 6/2011 | Francis et al. |
| D639,977 S | 6/2011 | Francis et al. |
| D640,389 S | 6/2011 | Francis et al. |
| 7,980,149 B2 | 7/2011 | Godfrey et al. |
| 7,985,560 B2 | 7/2011 | Vlakirs et al. |
| 8,017,339 B2 | 9/2011 | Piepenburg et al. |
| 8,022,194 B2 | 9/2011 | Piepenburg et al. |
| 8,024,148 B2 | 9/2011 | Petruno et al. |
| 8,029,982 B2 | 10/2011 | Kingsmore et al. |
| 8,030,000 B2 | 10/2011 | Piepenburg et al. |
| 8,038,965 B2 | 10/2011 | Keren |
| 8,039,783 B2 | 10/2011 | Lai |
| 8,043,867 B2 | 10/2011 | Petruno et al. |
| 8,062,850 B2 | 11/2011 | Piepenburg et al. |
| 8,062,901 B2 | 11/2011 | Dai et al. |
| 8,071,308 B2 | 12/2011 | Piepenburg et al. |
| 8,071,394 B2 | 12/2011 | Wu et al. |
| 8,084,224 B2 | 12/2011 | Buechler et al. |
| 8,114,612 B2 | 2/2012 | Buechler et al. |
| 8,128,871 B2 | 3/2012 | Petruno et al. |
| 8,129,191 B2 | 3/2012 | Sheard et al. |
| 8,153,381 B2 | 4/2012 | Palin et al. |
| D659,847 S | 5/2012 | Li |
| 8,486,717 B2 | 7/2013 | O'Farrell et al. |
| 2003/0073121 A1 | 4/2003 | Mendel-Hartvig et al. |
| 2003/0119202 A1 | 6/2003 | Kaylor et al. |
| 2004/0161365 A1 | 8/2004 | Yeung |
| 2005/0221504 A1 | 10/2005 | Petruno et al. |
| 2005/0221505 A1 | 10/2005 | Petruno et al. |
| 2005/0244953 A1 | 11/2005 | Cohen |
| 2006/0019265 A1 | 1/2006 | Song et al. |
| 2006/0172438 A1 | 8/2006 | Milunic et al. |
| 2006/0199278 A1 | 9/2006 | Leclipteux et al. |
| 2006/0223193 A1 | 10/2006 | Song et al. |
| 2006/0240541 A1 | 10/2006 | Petruno et al. |
| 2007/0048807 A1 | 3/2007 | Song |
| 2007/0141696 A1 | 6/2007 | Baugh et al. |
| 2007/0143035 A1 | 6/2007 | Petruno |
| 2007/0185679 A1 | 8/2007 | Petruno et al. |
| 2007/0211965 A1 | 9/2007 | Helbing et al. |
| 2008/0028261 A1 | 1/2008 | Petruno et al. |
| 2008/0069732 A1 | 3/2008 | Yi et al. |
| 2009/0047673 A1 | 2/2009 | Carey |
| 2009/0117006 A1 | 5/2009 | Fernandez |
| 2009/0157023 A1 | 6/2009 | Song et al. |
| 2009/0180925 A1 | 7/2009 | Petruno et al. |
| 2009/0180926 A1 | 7/2009 | Petruno et al. |
| 2009/0180927 A1 | 7/2009 | Petruno et al. |
| 2009/0180928 A1 | 7/2009 | Petruno et al. |
| 2009/0180929 A1 | 7/2009 | Petruno et al. |
| 2009/0214383 A1 | 8/2009 | Petruno et al. |
| 2009/0269858 A1 | 10/2009 | Punyadeera et al. |
| 2009/0311724 A1 | 12/2009 | Levison et al. |
| 2009/0325201 A1 | 12/2009 | Franzmann et al. |
| 2010/0015611 A1 | 1/2010 | Webster et al. |
| 2010/0081148 A1 | 4/2010 | Singbartl et al. |
| 2010/0094564 A1 | 4/2010 | Kuo et al. |
| 2010/0136585 A1 | 6/2010 | Schwind et al. |
| 2010/0143941 A1 | 6/2010 | Wu et al. |
| 2010/0165338 A1 | 7/2010 | Claps |
| 2010/0173423 A1 | 7/2010 | Zuaretz et al. |
| 2010/0239460 A1 | 9/2010 | Nazareth et al. |
| 2010/0240149 A1 | 9/2010 | Nazareth et al. |
| 2010/0255510 A1 | 10/2010 | Wang et al. |
| 2010/0279301 A1 | 11/2010 | Chinnaiyan et al. |
| 2010/0311181 A1 | 12/2010 | Abraham et al. |
| 2011/0003398 A1 | 1/2011 | Mendel-Hartvig et al. |
| 2011/0011959 A1 | 1/2011 | Greenwood et al. |
| 2011/0065136 A1 | 3/2011 | Labrie et al. |
| 2011/0065137 A1 | 3/2011 | LaBrie et al. |
| 2011/0065593 A1 | 3/2011 | Labrie et al. |
| 2011/0065598 A1 | 3/2011 | Labrie et al. |
| 2011/0065599 A1 | 3/2011 | LaBrie et al. |
| 2011/0065608 A1 | 3/2011 | LaBrie et al. |

(56) References Cited

U.S. PATENT DOCUMENTS

| | | | |
|---|---|---|---|
| 2011/0124519 | A1 | 5/2011 | Falkenberg et al. |
| 2011/0171754 | A1 | 7/2011 | Redmond et al. |
| 2012/0142023 | A1 | 6/2012 | Ascoli et al. |
| 2012/0184462 | A1 | 7/2012 | O'Farrell et al. |
| 2013/0225448 | A1 | 8/2013 | O'Farrell et al. |
| 2013/0225449 | A1 | 8/2013 | O'Farrell et al. |

FOREIGN PATENT DOCUMENTS

| | | |
|---|---|---|
| CN | 101151531 | 3/2008 |
| DE | 10 2006 060 066 | 6/2007 |
| DE | 10 2007 010 757 | 9/2007 |
| DE | 10 2007 044 889 | 4/2008 |
| EP | 0 149 168 | 7/1985 |
| EP | 0 250 137 | 12/1987 |
| EP | 0 323 605 | 7/1989 |
| EP | 1 459 068 | 9/2004 |
| EP | 1 582 598 | 10/2005 |
| EP | 1 666 879 | 6/2006 |
| EP | 2 666 018 | 11/2013 |
| GB | 1 526 708 | 9/1978 |
| WO | WO-99/40438 | 8/1999 |
| WO | WO-03/058242 | 7/2003 |
| WO | WO-2005/073733 | 8/2005 |
| WO | WO-2005/090987 | 9/2005 |
| WO | WO-2008/084331 | 7/2008 |
| WO | WO-2012/099897 | 7/2012 |
| WO | WO-2015/038978 | 3/2015 |

OTHER PUBLICATIONS

Response to Written Opinion with Chapter II Demand and Article 34 Amendments in PCT/US2013/050952, dated May 19, 2014, 17 pages.
Broach, et al., "High throughput screening for drug discovery," Nature (1996) 384:14-16.
Burbaum et al., "New technologies for high-throughput screening," Curr Opin Chem Biol. (1997) 1:72-78.
Dictionary definition of "adjacent", Merriam-Webster Online Dictionary (www.mw.com/dictionary/adjacent), dated Nov. 22, 2005.
E-mail from Elson Silva dated Jul. 19, 2012, 7 pages.
Fernandes et al., "Letter from the society president," J. Biomol. Screening (1997) 2:1.
Harlow et al., "Using Antibodies: A Laboratory Manual," p. 8 (Cold Spring Harbor Laboratory Press, Cold Springs Harbor, New York, 1999).
Illustration from Weiss Patent (U.S. Pat. No. 3,6431,235).
"Immunoglobulin D", Wikipedia, the free encyclopedia (en.wikipedia.org/wiki/IgD), dated Feb. 6, 2011.
"Immunoglobulin G", Wikipedia, the free encyclopedia (en.wikipedia.org/wiki/IgG), dated Feb. 6, 2011.
International Preliminary Report on Patentability for PCT/US12/21586, mailed Mar. 29, 2013.
International Search Report and Written Opinion for PCT/US2012/021586, mailed Apr. 19, 2012, 8 pages.
International Search Report and Written Opinion for PCT/US2012047493, mailed Oct. 1, 2012, 16 pages.
International Search Report and Written Opinion for PCT/US2012/047497, mailed Oct. 15, 2012, 12 pages.
International Search Report and Written Opinion for PCT/US2013/050952, mailed Oct. 17, 2013, 12 pages.
Janzen et al., "High throughput Screening as a Discovery Tool in the Pharmaceutical Industry," Lab Robotics Automation (1996) (8):261-265.
Leuvering et al., "Sole Particle Immunossay (SPIA)," J. Immunoassay (1980) 1(1):77-91.
Lexsee 365 F.2D 834, In re Griswold and Pearce, 365 F.2d 834 (1966).
Lexsee 417 F.3E 1369, *Pharmacia Corp. v. PAR Pharmaceutical, Inc.*, 417 F.3d 1369 (2005).

Office Action issued in U.S. Appl. No. 13/343,681, dated Aug. 20, 2012, 11 pages.
Request for Reexamination and Exhibits 1-5 for U.S. Pat. No. 6,805,837, dated Nov. 23, 2005.
Request for Reexamination and Exhibits 1-5 for U.S. Pat. No. 6,805,838, dated Nov. 23, 2005.
Request for Reexamination and Exhibits 1-3 for U.S. Pat. No. 5,073,484 dated Sep. 26, 2003.
Request for Reexamination and Exhibits 1-8 for U.S. Pat. No. 6,485,982 dated Sep. 15, 2005.
Requestor's Reply to Patent Owners Statement and Exhibits 1-2 for U.S. Pat. No. 6,805,837, dated Feb. 22, 2006.
Requestor's Reply to Patent Owners Statement and Exhibits 1-2 for U.S. Pat. No. 6,805,838, dated Feb. 22, 2006.
Restriction Requirement issued in U.S. Appl. No. 13/343,681, dated Apr. 9, 2012, 6 pages.
Response to Restriction Requirement in U.S. Appl. No. 13/343,681, dated Apr. 27, 2012, 9 pages.
Statement by Patent Owner and Exhibits A-D for U.S. Pat. No. 6,805,837, dated Dec. 23, 2005.
Statement by Patent Owner and Exhibits A-D for U.S. Pat. No. 6,805,838, dated Dec. 23, 2005.
Takeda et al., "Experience in Use of Urotrace for Urine of Patients," Rinsho Kensa (Clinical Test) (1974) (original article in Japanese followed by Engiish translation).
ThermoFisher Scientific information sheet entitled "Color-Rich™ Fluoro-Max™ Dyed Microparticles," dated Mar. 2008.
Thermo Scientific Instructions sheet entitled Dylight™ Microscale Antibody Labeling Kits,: copyrighted 2010.
Van Hell et al., in Alternative Immunoassays (W.P. Collins ed., John Wiley & Sons, 1985), Ch. 4 "Particle Immunoassays," pp. 39-59.
Wood et al., "Base composition-independent hybridization in tetramethylammonium chloride: a method for oligonucleotide screening of highly complex gene libraries," Proc Natl Acad Sci USA (1985) 82(6):1585-1588.
Carter et al., "Lateral flow microarrays: a novel platform for rapid nucleic acid detection based on miniaturized lateral flow chromatography," Nucleic Acids Research (2007) 35(10):e74.
Communication pursuant to Rule 114(2) EPC for Application No. 12 709 406.8 dated Dec. 1, 2015.
Communication pursuant to Article 94(3) EPC for EP 12709406.8, dated Apr. 20, 2015, 5 pages.
Examination Report in European Patent Application No. EP12709406.8, dated Jul. 16, 2014, 5 pages.
First Office Action in Chinese Patent Application No. 201280005790.1, dated Oct. 15, 2014, 18 pages (English language summary included).
Gantelius et al., "A lateral flow protein microarray for rapid determination of contagious bovine pleuropneumonia status in bovine serum," J Microbiol Methods (2010) 82(1):11-8.
International Preliminary Report on Patentability for PCT/US14/55520, dated Sep. 30, 2015.
International Preliminary Report on Patentability for PCT/US2014/055520, dated Dec. 1, 2014.
Invitation Pursuant to Rule 137(4) EPC in European Patent Application No. EP12709406.8, dated May 21, 2014, 2 pages.
Notice of First Office Action for CN 201380046764.8, dated Oct. 10, 2015.
Response to Communication pursuant to Art. 94(3) EPC dated Oct. 30, 2015, 10 pages.
Response to Office Action in European Patent Application No. EP12709406.8, dated Mar. 14, 2014, 7 pages.
Response to Rule 137(4) EPC in European Patent Application No. EP12709406.8, dated Jun. 30, 2014, 3 pages.
Response to the First Office Action for CN 201280005790.1, filed Mar. 30, 2015, 27 pages.
Response to Office Action in U.S. Appl. No. 13/343,681, dated Apr. 12, 2013, 8 pages.
Second Office Action (translation) for CN 201280005790.1, dated May 27, 2015, 3 pages.
Summons to attend oral proceedings pursuant to rule 115(1) EPC for Application No. 12 709 406.8, dated Dec. 10, 2015.

(56) References Cited

OTHER PUBLICATIONS

Taranova et al., "Integration of lateral flow and microarray technologies for multiplex immunoassay: application to the determination of drugs of abuse," Microchim Acta (2013) 180:1165-1172.
Response to Notice of First Office Action for CN 201380046764.8, filed Feb. 25, 2016, 11 pages.
Notification of Second Office Action for CN 201380046764.8, dated May 26, 2016, 6 pages.
Response to Notification of Second Office Action for CN 201380046764.8, filed Sep. 9, 2016, 9 pages.
Notification of Third Office Action for CN 201380046764.8, dated Jan. 10, 2017, 10 pages.
Response to Notification of Third Office Action for CN 201380046764.8, filed Mar. 27, 2017, 10 pages.
Non-final Rejection for U.S. Appl. No. 13/862,301, dated Jun. 30, 2016, 13 pages.
Response to Non-final Rejection for U.S. Appl. No. 13/862,301, filed Dec. 30, 2016, 17 pages.
Notice of Allowance for U.S. Appl. No. 14/485,283, dated Jul. 8, 2016, 9 pages.
Request for Continued Examination for U.S. Appl. No. 14/485,283, filed Oct. 7, 2016, 3 pages.
Communication pursuant to Article 94(3) EPC for EP 12 709 406.8, dated Apr. 18, 2016, 3 pages.
Response to Communication pursuant to Article 94(3) EPC for EP 12 709 406.8, filed Jun. 27, 2016, 71 pages.
Communication under Rule 71(3) EPC for EP 12 709 406.8, dated Oct. 11, 2016, 95 pages.
Decision to grant for EP 12 709 406.8, dated Mar. 9, 2017, 2 pages.
Notice of Allowance for U.S. Appl. No. 14/485,283, dated Nov. 3, 2016, 9 pages.
Response to Notice of Allowance for U.S. Appl. No. 14/485,283, dated Feb. 3, 2017, 14 pages.
Non-final Rejection for U.S. Appl. No. 13/862,313, dated Jul. 1, 2016, 13 pages.
Response to Non-final Rejection for U.S. Appl. No. 13/862,313, filed Dec. 30, 2016, 15 pages.
Notice of Allowance for U.S. Appl. No. 13/862,313, dated Apr. 11, 2017, 11 pages.
Extended European Search Report for EP 17157319.9, dated Apr. 7, 2017, 9 pages.
Notice of Allowance for U.S. Appl. No. 13/862,301, dated Apr. 7, 2017, 13 pages.
Request for Continued Examination for U.S. Appl. No. 13/862,301, dated Jul. 6, 2017, 3 pages.
Notice of Granting Patent Right for CN 201380046764.8, dated Jun. 2, 2017, 3 pages (Including English translation).
Notice of the First Office Action for CN 201480058016.6, dated Mar. 15, 2017, 9 pages (Including English translation).
Request for Continued Examination for U.S. Appl. No. 13/862,313, dated Jul. 7, 2017, 3 pages.

\* cited by examiner

LATERAL FLOW ASSAYS USING TWO DIMENSIONAL FEATURES

I. CROSS-REFERENCE TO RELATED APPLICATIONS

This application claims the priority benefit of U.S. provisional application Ser. No. 61/673,156, filed Jul. 18, 2012, the content of which is incorporated by reference in its entirety.

II. TECHNICAL FIELD

The present invention relates to novel lateral flow devices using two dimensional features, preferably, uniform two dimensional test and control features, to provide for flow control information, to function as an internal control and/or to provide for internal calibration information for the test device. The present invention also relates to methods for using the lateral flow devices to provide for flow control information, to function as an internal control and/or to provide for internal calibration information for the test device.

III. BACKGROUND OF THE INVENTION

Lateral flow assays have been developed and used for various purposes. There is a need for lateral flow assays with improved or more complete control and/or calibration features. The present invention addresses this and related needs in the art.

IV. DISCLOSURE OF THE INVENTION

In one aspect, the present disclosure provides for a test device, which device comprises a plurality of reagent dots on a matrix, wherein at least two of said reagent dots do not overlap and are sufficiently spaced apart from each other so that when a liquid flows laterally along said matrix, flow of said liquid to, through and/or around one of said two reagent dots does not substantially affect flow of said liquid sample to, through and/or around said other reagent dot, each of said two reagent dots is neither a reagent line across the entire width of said matrix in a direction perpendicular to the direction of said liquid flow nor a complete circle of a reagent line circulating the center or sample or liquid application site of said test device, and after a liquid flows laterally along said test device and passes said at least two reagent dots, detectable signals are formed at said at least two reagent dots to provide for flow control information, to function as an internal control and/or to provide for internal calibration information for said test device.

In another aspect, the present disclosure provides for a method, which method comprises: a) contacting a liquid with the above test device, wherein the liquid is applied to a site of said test device upstream of said at least two reagent dots; b) transporting a labeled reagent to said at least two reagent dots; and c) assessing the presence, absence, amount and/or pattern of signal(s) generated by said labeled reagent at said at least two reagent dots to provide for flow control information, to function as an internal control and/or to provide for internal calibration information for said test device.

In some embodiments, the present test devices can further comprise a detection site to indicate presence, absence and/or amount of an analyte in a liquid sample, and the present methods can be used to further indicate presence, absence and/or amount of an analyte in a liquid sample. Any suitable designs or devices, including the designs or devices disclosed and/or claimed in U.S. provisional application Ser. No. 61/461,499, filed Jan. 18, 2011, U.S. patent application Ser. No. 13/343,681, filed Jan. 4, 2012, and international patent application No. PCT/US2012/021586, filed Jan. 17, 2012, can be combined with the present designs or devices to form a device to provide for flow control information, to function as an internal control and/or to provide for internal calibration information for the test device, and to indicate presence, absence and/or amount of an analyte in a liquid sample. Similarly, the present methods can also incorporate the methods disclosed and/or claimed in U.S. provisional application Ser. No. 61/461,499, filed Jan. 18, 2011, U.S. patent application Ser. No. 13/343,681, filed Jan. 4, 2012, and international patent application No. PCT/US2012/021586, filed Jan. 17, 2012, to provide for flow control information, an internal control and/or internal calibration information for the test device, and to indicate presence, absence and/or amount of an analyte in a liquid sample.

The principles of the present test devices and methods can be applied, or can be adapted to apply, to the lateral flow test devices and assays known in the art. For example, the principles of the present test devices and methods can be applied, or can be adapted to apply, to the lateral flow test devices and assays disclosed and/or claimed in the U.S. Pat. Nos. 3,641,235, 3,959,078, 3,966,897, 4,094,647, 4,168,146, 4,299,916, 4,347,312, 4,366,241, 4,391,904, 4,425,438, 4,517,288, 4,960,691, 5,141,875, 4,857,453, 5,073,484, 4,695,554, 4,703,017, 4,743,560, 5,075,078, 5,591,645, 5,656,448, RE 38,430 E, 5,602,040, 6,017,767, 6,319,676, 6,352,862, 6,485,982, 5,120,643, 4,956,302, RE 39,664 E, 5,252,496, 5,514,602, 7,238,538 B2, 7,175,992 B2, 6,770,487 B2, 5,712,170, 5,275,785, 5,504,013, 6,156,271, 6,187,269, 6,399,398, 7,317,532, EP 0,149,168 A1, EP 0,323,605 A1, EP 0,250,137 A2, GB 1,526,708 and WO99/40438.

V. BRIEF DESCRIPTION OF THE DRAWINGS

Figure 1B:
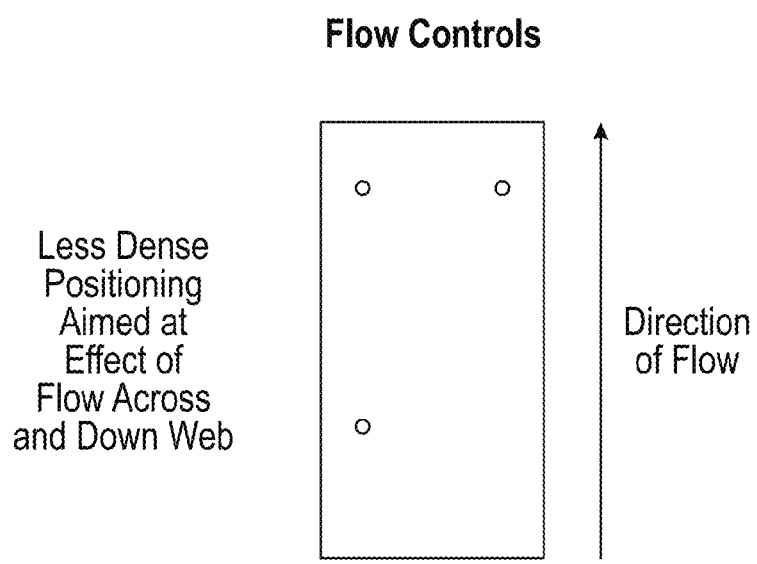
Figure 1C:
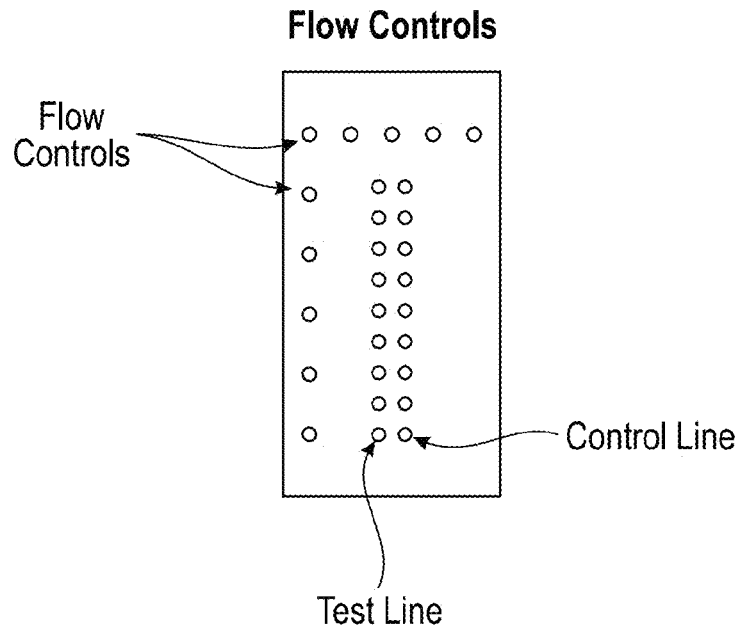

FIGS. 1A-C illustrate several exemplary assays with flow control features. As illustrated in these figures, analyte dependent control features along, across and/or within the flow field can account for mechanical variations in test performance within the field. In some embodiments, the binding features can also be analyte independent control features. In both cases, the control features can be placed or painted on the actual test being run and the signals at the control features can be evaluated at the read time of the test. Alternatively, kinetic measurements can also be used.

Figure 2:
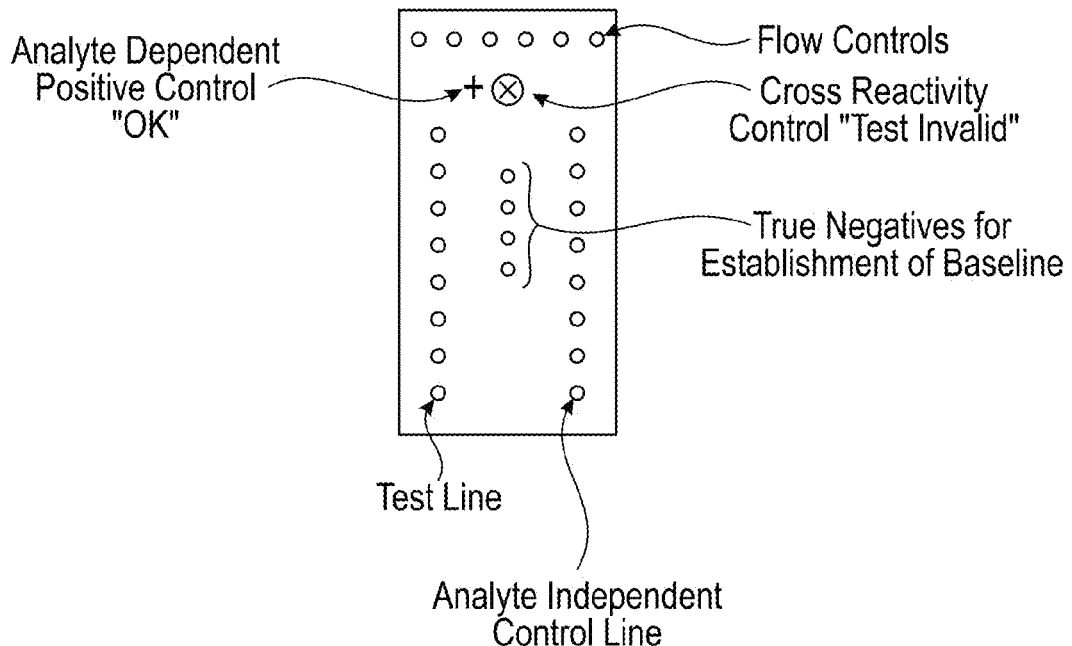

FIG. 2 illustrates an exemplary assay with intended positive or negative control features. As illustrated in this figure, the exemplary assay includes a true negative control feature, a control feature for cross reactivity, and an analyte dependent positive control feature.

Figures 1, 3A:
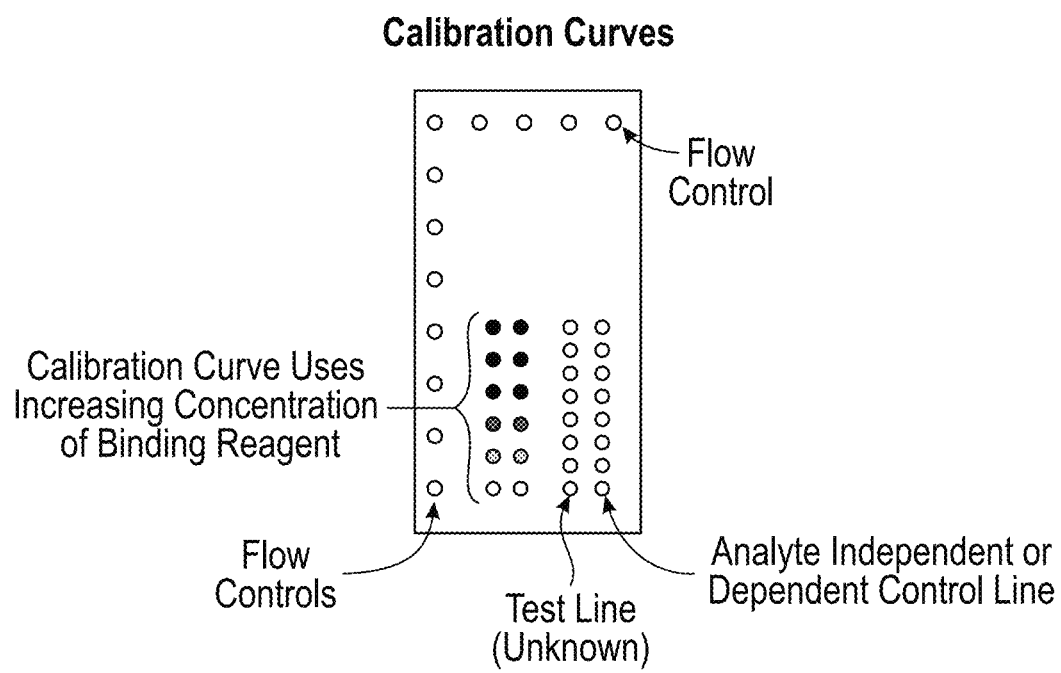
Figures 2, 3A:
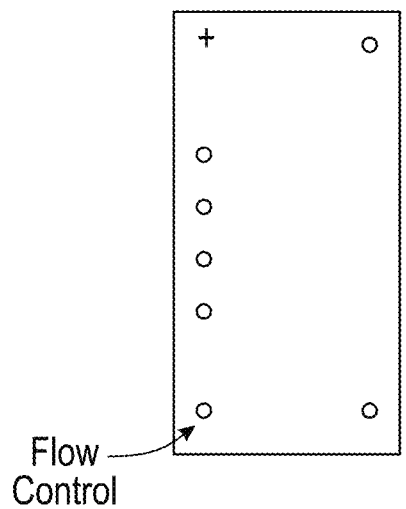

FIGS. 3A-1 and 3A-2 illustrate exemplary assays with analyte independent calibration features. The calibration features can be used for reader calibration. The calibration features can be a relatively complex curve as shown in the top example, FIG. 3A-1, or relatively simple features of known binding characteristics as shown in the bottom example, FIG. 3A-2.

Figures 1, 3B:
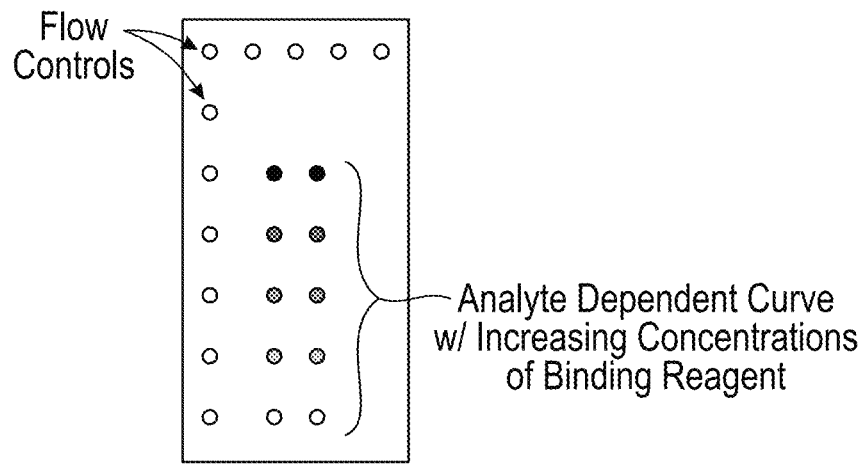
Figures 2, 3B:
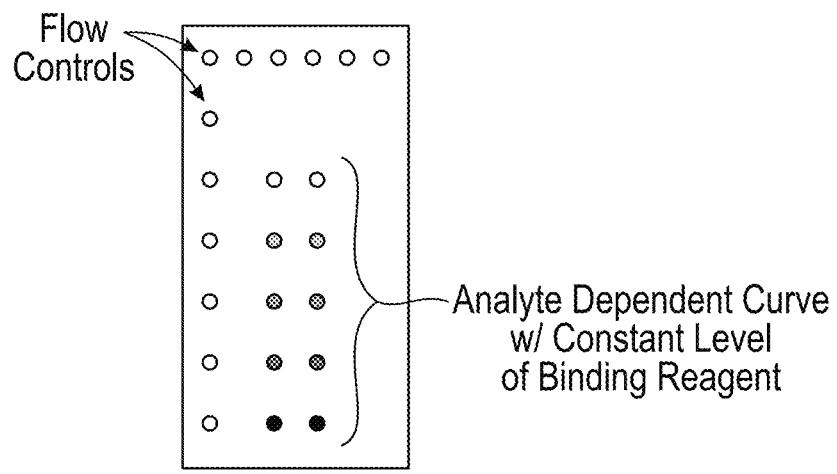

FIGS. 3B-1 and 3B-2 illustrate exemplary assays with analyte dependent calibration features. The top example, FIG. 3B-1, illustrates an analyte dependent calibration curve wherein excess amount of analyte can be run and the signal strength can be modulated by increasing concentrations of the binding reagent(s) in the calibration curve. The bottom example, FIG. 3B-2, illustrates an analyte dependent calibration curve containing constant level of the binding reagent(s). Analyte can be run against multiple devices with different levels of the binding reagent(s) to establish different binding patterns across a desired range of the test devices.

VI. DETAILED DESCRIPTION OF THE INVENTION

A. Definitions

Unless defined otherwise, all technical and scientific terms used herein have the same meaning as is commonly understood by one of ordinary skill in the art to which this invention belongs. All patents, patent applications (published or unpublished), and other publications referred to herein are incorporated by reference in their entireties. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, "a line that is substantially parallel to the liquid flow direction" means that the angle between the line and the liquid flow direction is at least less than 45 degrees or more than 135 degrees. In some specific embodiments, the angle between the line and the liquid flow direction is at about 40, 35, 30, 25, 20, 15, 10, 5, 4, 3, 2, or 1 degree, or the line is completely parallel to the liquid flow direction. In other specific embodiments, the angle between the line and the liquid flow direction is at about 140, 145, 150, 155, 160, 165, 170, 175, 176, 177, 178, or 179 degrees, or the line is completely parallel to the liquid flow direction.

As used herein, "a line is substantially perpendicular to the liquid flow direction" means that the angle between the line and the liquid flow direction is at least more than 45 degrees or less than 135 degrees. In some specific embodiments, the angle between the line and the liquid flow direction is at about 50, 55, 60, 65, 70, 75, 80, 85, 86, 87 88 or 89 degrees, or the line is completely perpendicular to the liquid flow direction. In other specific embodiments, the angle between the line and the liquid flow direction is at about 130, 125, 120, 115, 110, 105, 100, 95, 94, 93, 92 or 91 degrees, or the line is completely perpendicular to the liquid flow direction.

As used herein, "reagent dots have substantially the same size or diameter" means that the difference in the size or diameter between the largest dot and smallest dot is not more than one fold or less than 50% of the average or median size or diameter of the reagent dots. In some specific embodiments, the difference in the size or diameter between the largest dot and smallest dot is within 45%, 40%, 30%, 20%, 10%, 5%, or 1% of the average or median size or diameter of the reagent dots. In other specific embodiments, reagent dots have he same size or diameter.

As used herein, "the distance between reagent dots is substantially the same" means that the distance between or among reagent dots, often adjacent reagent dots, is within 50% variation of the average or median distance between or among reagent dots or adjacent reagent dots. In some specific embodiments, the distance between or among reagent dots or adjacent reagent dots is within 45%, 40%, 30%, 20%, 10%, 5%, or 1% variation of the average or median distance between or among reagent dots or adjacent reagent dots. In other specific embodiments, the distance between or among reagent dots is the same. Such space or distance can be measured by any suitable means. In some specific embodiments, the space or distance between or among reagent dots is measured as the space or distance between or among the edges of the reagent dots or adjacent reagent dots. In other specific embodiments, the space or distance between or among reagent dots is measured as the space or distance between or among the centers or effective centers of the reagent dots or adjacent reagent dots.

As used herein, a "binding reagent" refers to any substance that binds to a target or an analyte with desired affinity and/or specificity. Non-limiting examples of the binding reagent include cells, cellular organelles, viruses, particles, microparticles, molecules, or an aggregate or complex thereof, or an aggregate or complex of molecules. Exemplary binding reagents can be an amino acid, a peptide, a protein, e.g., an antibody or receptor, a nucleoside, a nucleotide, an oligonucleotide, a nucleic acid, e.g., DNA or RNA, a vitamin, a monosaccharide, an oligosaccharide, a carbohydrate, a lipid, an aptamer and a complex thereof.

As used herein, "antibody" includes not only intact polyclonal or monoclonal antibodies, but also fragments thereof (such as Fab, Fab', F(ab')$_2$, Fv), single chain (ScFv), a diabody, a multi-specific antibody formed from antibody fragments, mutants thereof, fusion proteins comprising an antibody portion, and any other modified configuration of the immunoglobulin molecule that comprises an antigen recognition site of the required specificity. An antibody includes an antibody of any class, such as IgG, IgA, or IgM (or sub-class thereof), and the antibody need not be of any particular class As used herein, "monoclonal antibody" refers to an antibody obtained from a population of substantially homogeneous antibodies, i.e., the antibodies comprising the population are identical except for possible naturally occurring mutations that are present in minor amounts. As used herein, a "monoclonal antibody" further refers to functional fragments of monoclonal antibodies.

As used herein, the term "specifically binds" refers to the specificity of a binding reagent, e.g., an antibody, such that it preferentially binds to a defined analyte or target. Recognition by a binding reagent or an antibody of a particular analyte or target in the presence of other potential targets or interfering substances is one characteristic of such binding. In some embodiments, a binding reagent that specifically binds to an analyte or target avoids binding to other interfering moiety or moieties in the sample to be tested.

As used herein the term "avoids binding" refers to the specificity of particular binding reagents, e.g., antibodies or antibody fragments. Binding reagents, antibodies or antibody fragments that avoid binding to a particular moiety generally contain a specificity such that a large percentage of the particular moiety would not be bound by such binding reagents, antibodies or antibody fragments. This percentage generally lies within the acceptable cross reactivity percentage with interfering moieties of assays utilizing the binding reagents or antibodies directed to detecting a specific target. Frequently, the binding reagents, antibodies or antibody fragments of the present disclosure avoid binding greater than about 90% of an interfering moiety, although higher percentages are clearly contemplated and preferred. For example, binding reagents, antibodies or antibody fragments of the present disclosure avoid binding about 91%, about 92%, about 93%, about 94%, about 95%, about 96%, about 97%, about 98%, about 99%, and about 99% or more of an interfering moiety. Less occasionally, binding reagents, antibodies or antibody fragments of the present disclosure avoid binding greater than about 70%, or greater than about 75%, or greater than about 80%, or greater than about 85% of an interfering moiety.

As used herein, "mammal" refers to any of the mammalian class of species. Frequently, the term "mammal," as used herein, refers to humans, human subjects or human patients.

As used herein, the term "subject" is not limited to a specific species or sample type. For example, the term "subject" may refer to a patient, and frequently a human patient. However, this term is not limited to humans and thus encompasses a variety of mammalian species.

As used herein the term "sample" refers to anything which may contain an analyte for which an analyte assay is desired. The sample may be a biological sample, such as a biological fluid or a biological tissue. Examples of biological fluids include urine, blood, plasma, serum, saliva, semen, stool, sputum, cerebral spinal fluid, tears, mucus, amniotic fluid or the like. Biological tissues are aggregate of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s).

As used herein, "stringency" of nucleic acid hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured nucleic acid sequences to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Current Protocols in Molecular Biology (Ausubel et al. eds., Wiley Interscience Publishers, 1995); Molecular Cloning: A Laboratory Manual (J. Sambrook, E. Fritsch, T. Maniatis eds., Cold Spring Harbor Laboratory Press, 2d ed. 1989); Wood et al., *Proc. Natl. Acad. Sci. USA,* 82:1585-1588 (1985).

As used herein the term "isolated" refers to material removed from its original environment, and is altered from its natural state. For example, an isolated polypeptide could be coupled to a carrier, and still be "isolated" because that polypeptide is not in its original environment.

As used herein, "test substance (or candidate compound)" refers to a chemically defined compound (e.g., organic molecules, inorganic molecules, organic/inorganic molecules, proteins, peptides, nucleic acids, oligonucleotides, lipids, polysaccharides, saccharides, or hybrids among these molecules such as glycoproteins, etc.) or mixtures of compounds (e.g., a library of test compounds, natural extracts or culture supernatants, etc.) whose effect on a target is determined by the disclosed and/or claimed methods herein.

As used herein, high-throughput screening (HTS) refers to processes that test a large number of samples, such as samples of diverse chemical structures against disease targets to identify "hits" (see, e.g., Broach, et al., High throughput screening for drug discovery, *Nature,* 384:14-16 (1996); Janzen, et al., High throughput screening as a discovery tool in the pharmaceutical industry, *Lab Robotics Automation:* 8261-265 (1996); Fernandes, P. B., Letter from the society president, *J. Biomol. Screening,* 2:1 (1997); Burbaum, et al., New technologies for high-throughput screening, *Curr. Opin. Chem. Biol.,* 1:72-78 (1997)). HTS operations are highly automated and computerized to handle sample preparation, assay procedures and the subsequent processing of large volumes of data.

As used herein, "plant" refers to any of various photosynthetic, eucaryotic multi-cellular organisms of the kingdom Plantae, characteristically producing embryos, containing chloroplasts, having cellulose cell walls and lacking locomotion.

As used herein, "animal" refers to a multi-cellular organism of the kingdom of Animalia, characterized by a capacity for locomotion, nonphotosynthetic metabolism, pronounced response to stimuli, restricted growth and fixed bodily structure. Non-limiting examples of animals include birds such as chickens, vertebrates such fish and mammals such as mice, rats, rabbits, cats, dogs, pigs, cows, ox, sheep, goats, horses, monkeys and other non-human primates.

As used herein, "bacteria" refers to small prokaryotic organisms (linear dimensions of around 1 micron) with non-compartmentalized circular DNA and ribosomes of about 70S. Bacteria protein synthesis differs from that of eukaryotes. Many anti-bacterial antibiotics interfere with bacteria proteins synthesis but do not affect the infected host.

As used herein, "eubacteria" refers to a major subdivision of the bacteria except the archaebacteria. Most Gram-positive bacteria, cyanobacteria, mycoplasmas, enterobacteria, pseudomonas and chloroplasts are eubacteria. The cytoplasmic membrane of eubacteria contains ester-linked lipids; there is peptidoglycan in the cell wall (if present); and no introns have been discovered in eubacteria.

As used herein, "archaebacteria" refers to a major subdivision of the bacteria except the eubacteria. There are three main orders of archaebacteria: extreme halophiles, methanogens and sulphur-dependent extreme thermophiles. Archaebacteria differs from eubacteria in ribosomal structure, the possession (in some case) of introns, and other features including membrane composition.

As used herein, "virus" refers to an obligate intracellular parasite of living but non-cellular nature, consisting of DNA or RNA and a protein coat. Viruses range in diameter from about 20 to about 300 nm. Class I viruses (Baltimore classification) have a double-stranded DNA as their genome; Class II viruses have a single-stranded DNA as their genome; Class III viruses have a double-stranded RNA as their genome; Class IV viruses have a positive single-stranded RNA as their genome, the genome itself acting as mRNA; Class V viruses have a negative single-stranded RNA as their genome used as a template for mRNA synthesis; and Class VI viruses have a positive single-stranded RNA genome but with a DNA intermediate not only in replication but also in mRNA synthesis. The majority of viruses are recognized by the diseases they cause in plants, animals and prokaryotes. Viruses of prokaryotes are known as bacteriophages.

As used herein, "fungus" refers to a division of eucaryotic organisms that grow in irregular masses, without roots, stems, or leaves, and are devoid of chlorophyll or other pigments capable of photosynthesis. Each organism (thallus) is unicellular to filamentous, and possesses branched somatic structures (hyphae) surrounded by cell walls containing glucan or chitin or both, and containing true nuclei.

B. Lateral Flow Devices Using Two Dimensional Features

In one aspect, the present disclosure provides for a test device, which device comprises a plurality of reagent dots on a matrix, wherein at least two of said reagent dots do not overlap and are sufficiently spaced apart from each other so that when a liquid flows laterally along said matrix, flow of said liquid to, through and/or around one of said two reagent dots does not substantially affect flow of said liquid sample to, through and/or around said other reagent dot, each of said two reagent dots is neither a reagent line across the entire width of said matrix in a direction perpendicular to the direction of said liquid flow nor a complete circle of a reagent line circulating the center or sample or liquid application site of said test device, and after a liquid flows laterally along said test device and passes said at least two reagent dots, detectable signals are formed at said at least two reagent dots to provide for flow control information, to function as an internal control and/or to provide for internal calibration information for said test device.

In some embodiments, the detectable signals are formed at the at least two reagent dots to provide for flow control information for the test device. The present devices can be used to provide for any suitable flow control information. For example, the flow control information can allow internal calibration within the test device for perturbation in test results caused by variability in flow rate or flow pattern laterally across the surface and/or along the length of the flow field.

In some embodiments, the present test devices can further comprise a detection site to indicate presence, absence and/or amount of an analyte in a liquid sample. Any suitable designs or devices, including the designs or devices disclosed and/or claimed in U.S. provisional application Ser. No. 61/461,499, filed Jan. 18, 2011, U.S. patent application Ser. No. 13/343,681, filed Jan. 4, 2012, and international patent application No. PCT/US2012/021586, filed Jan. 17, 2012, can be combined with the present designs or devices to form a device to provide for flow control information, to function as an internal control and/or to provide for internal calibration information for the test device, and to indicate presence, absence and/or amount of an analyte in a liquid sample.

In some embodiments, the present test devices can further comprise a plurality of reagent dots on a matrix, wherein at least two of said reagent dots do not overlap and are sufficiently spaced apart from each other so that when said liquid sample flows laterally along said matrix, flow of said liquid sample to, through and/or around one of said two reagent dots does not substantially affect flow of said liquid sample to, through and/or around said other reagent dot, each of said two reagent dots is neither a reagent line across the entire width of said matrix in a direction perpendicular to the direction of said liquid sample flow nor a complete circle of a reagent line circulating the center or sample or liquid application site of said test device, and after a liquid sample flows laterally along said test device and passes said at least two reagent dots, said at least two reagent dots form a predetermined pattern to indicate presence, absence and/or amount of said analyte in said liquid sample.

The detectable signals at the least two reagent dots can be formed in any suitable manner. For example, the formation of the detectable signals at the at least two reagent dots can be independent from the presence, absence and/or amount of the analyte in a liquid sample. In some embodiments, each of the at least two reagent dots can comprise a reagent that binds to a labeled binding reagent for the analyte, and the reagent dots can be used to form the detectable signals at the at least two reagent dots independently from the presence, absence and/or amount of the analyte in a liquid sample. In other embodiments, the reagent at each of the at least two reagent dots can comprise an analyte or analyte analog, and the analyte or analyte analog can be used to form the detectable signals at the at least two reagent dots independently from the presence, absence and/or amount of the analyte in a liquid sample.

In another example, the formation of the detectable signals at the at least two reagent dots can depend on the presence and/or amount of the analyte or a non-analyte substance in a liquid sample. In some embodiments, each of the at least two reagent dots can comprise a reagent that binds to the analyte, and the reagents can be used to form the detectable signals at the reagent dots that are dependent on the presence, absence and/or amount of the analyte in a liquid sample. In other embodiments, each of the at least two reagent dots can comprise a reagent that binds to the non-analyte substance, and the reagents can be used to form the detectable signals at the reagent dots that are dependent on the presence, absence and/or amount of the non-analyte substance in a liquid sample.

The reagent dots can form any suitable pattern to provide for flow control information, to function as an internal control and/or to provide for internal calibration information for the test device. In some embodiments, the at least two reagent dots form a line that is substantially parallel to the liquid flow direction, a line that is substantially perpendicular to the liquid flow direction and/or a line that is at a predetermined angle relative to the liquid flow direction.

In some embodiments, each of the at least two reagent dots comprises the same or different reagent(s). In other embodiments, each of the at least two reagent dots comprises the same amount of the reagent. In still other embodiments, the at least two reagent dots comprise different amounts of the reagent.

In some embodiments, the detectable signal is formed at one or more of the at least two reagent dots to function as an internal control for the test device. For example, the detectable signal can be formed at a single reagent dot to function as an internal control for the test device. In another example, the detectable signals can be formed at a plurality of reagent dots to function as an internal control for the test device.

The detectable signal can be formed at one or more of the at least two reagent dots to function as any suitable types of internal control. In some embodiments, the internal control can be an internal control for cross reactivity or an interfering substance, an internal positive control, and/or an internal negative control. In other embodiments, the internal control can be an internal control for cross reactivity or an interfering substance.

Any suitable reagent(s) can be used to function as the internal control for cross reactivity or an interfering substance. In some embodiments, the reagent dot that functions as the internal control for cross reactivity or an interfering substance comprises a reagent for binding to an analyte analog or an interfering substance that is known or likely to be present in a testing sample.

The detectable signal can form a predetermined pattern indicating the presence and/or amount of cross reactivity or an interfering substance in a testing sample. In some embodiments, a plurality of the reagent dots function as the internal control for cross reactivity or an interfering substance. In other embodiments, a single reagent dot functions as the internal control for cross reactivity or an interfering substance.

In some embodiments, the internal control is an internal positive control. The detectable signals at the at least two reagent dots can be formed in any suitable manner. For example, the formation of the detectable signal(s) at the reagent dot(s) can depend on the presence and/or amount of the analyte and/or a non-analyte substance in a liquid sample. Any suitable reagent can be used to function as the internal positive control. For example, the reagent dot that functions as the internal positive control can comprise a reagent for binding to an analyte or a non-analyte substance.

In some embodiments, the detectable signal can form a predetermined pattern indicating the analyte or a non-analyte substance in a testing sample. In other embodiments, a plurality of the reagent dots function as the internal positive controls. The plurality of the reagent dots can be used for any suitable purposes. For example, the signals at the plurality of the reagent dots can comprise constant intensity or varying intensities at various locations.

In some embodiments, the internal control is an internal negative control. An internal negative control can be formed in any suitable manner. For example, the reagent dot can be treated as the same for a test site except that a regent for binding to an analyte is not applied to the reagent dot to function as an internal negative control.

In some embodiments, a plurality of the reagent dots can function as the internal negative controls.

In some embodiments, the detectable signals are formed at the at least two reagent dots to provide for internal calibration information for the test device. The detectable signals can be formed in any suitable manner to provide for internal calibration information for the test device. In some embodiments, the formation of the detectable signals at the at least two reagent dots can be independent from the presence, absence and/or amount of the analyte in a liquid sample. For example, each of the at least two reagent dots can comprise a reagent that binds to a labeled binding reagent for the analyte, and the reagents can be used to form the detectable signals at the reagent dots that are independent from the presence, absence and/or amount of the analyte in a liquid sample. In another example, the reagent at each of the at least two reagent dots can comprise an analyte or analyte analog, and the reagents can be used to form the detectable signals at the reagent dots that are independent from the presence, absence and/or amount of the analyte in a liquid sample.

In some embodiments, the detectable signals are formed at the at least two reagent dots to provide internal calibration information for the desired analyte testing range.

The reagent dots can form any suitable pattern to provide for internal calibration information for the test device. In some embodiments, the at least two reagent dots form a line that is substantially parallel to the liquid flow direction, a line that is substantially perpendicular to the liquid flow direction and/or a line that is at a predetermined angle relative to the liquid flow direction. In other embodiments, the detectable signals at the reagent dots form a gradient of signal strength in a direction of the line formed by the reagent dots.

In some embodiments, the test device does not comprise a detection site to indicate presence, absence and/or amount of an analyte in a liquid sample and the detectable signals are formed at the at least two reagent dots to provide for internal calibration information for the test device. The detectable signals can be formed in any suitable manner to provide for internal calibration information for the test device. In some embodiments, the formation of the detectable signals at the at least two reagent dots depends on the presence and/or amount of the analyte in a calibration liquid. For example, each of the at least two reagent dots can comprise a reagent that binds to the analyte, and the reagent dots can be used to provide for internal calibration information.

In some embodiments, the detectable signals can be formed at the least two reagent dots to provide for internal calibration information for the desired analyte testing ranging.

The reagent dots can form any suitable pattern to provide for internal calibration information for the test device. In some embodiments, the at least two reagent dots form a line that is substantially parallel to the liquid flow direction, a line that is substantially perpendicular to the liquid flow direction and/or a line that is at a predetermined angle relative to the liquid flow direction. In other embodiments, the detectable signals at the reagent dots form a gradient of signal strength in a direction of the line formed by the reagent dots.

In some embodiments, each of the at least two reagent dots comprises a reagent that binds to the analyte and the amount of the reagent forms a gradient in a direction of the line for the reagent dots. The detectable signal at the reagent dots can be the same for a predetermined level of analyte in a calibration liquid In some embodiments, the test device does not comprise a detection site to indicate presence, absence and/or amount of an analyte in a liquid sample and the at least two reagent dots comprise a binding reagent that is adopted to generate signals of specific signal strengths relative to one another or absolute signal strengths of differing levels. The reagent dots can form any suitable pattern to provide for internal calibration information for the test device. In some embodiments, the at least two reagent dots form a line that is substantially parallel to the liquid flow direction, a line that is substantially perpendicular to the liquid flow direction and/or a line that is at a predetermined angle relative to the liquid flow direction.

In some embodiments, the detectable signals are formed at the at least two reagent dots to provide for or to function at least two of the following: 1) to provide for flow control information; 2) to function as an internal control; and 3) to provide for internal calibration information for the test device. In other embodiments, the detectable signals are formed to provide for flow control information, to function as an internal control and to provide for internal calibration information for the test device.

Numerous variables can be considered to make the test device to ensure that the reagent dots do not overlap and are sufficiently spaced apart from each other so that liquid flow to, through and/or around one reagent dot or set of reagent dots does not substantially affect flow of the liquid flow to, through and/or around other reagent dot or other sets of reagent dots. And at the same time, the test device should comprise sufficient number of the reagent dots that can be used in generating signal readout to provide for flow control information, to function as an internal control and/or to provide for internal calibration information for the test device, and sometimes to indicate presence, absence and/or amount of the analyte in the liquid sample. Exemplary variables that can be considered and/or adjusted in making the test device include the number of reagent dots, the size and/or shape of the reagent dots, e.g., whether the absolute size or the size relative to the size of the matrix, the types and amounts of the reagents located at the reagent dots, the spacing between or among a portion or all reagent dots on the test device, e.g., whether the absolute size of the spacing or the size of the spacing relative to the size of the matrix and/or the number of the reagent dots on the matrix, the orientation or position of the reagent dots relative to the liquid flow direction, the uniformity or variations of the sizes and/or shape among the reagent dots and the properties of the matrix, e.g., the material and/or porosity of the matrix, and/or the properties or composition of the solution in which the reagent is spotted. Some or all of these variables can be tested, adjusted or determined to make a test device that meets the intended test performance, e.g., meeting the intended or desired assay sensitivity and/or specificity.

In some specific embodiments, it can be determined that the reagent dots do overlap and are not sufficiently spaced apart from each other so that liquid flow to, through and/or around one reagent dot or set of reagent dots blocks or prevents flow of the liquid flow to, through and/or around other reagent dot or other sets of reagent dots. Some or all of these variables can then be adjusted so that the liquid flow blocking effect be reduced by at least 10%, and preferably by at least 20%, 30%, 40%, 50%, 60%, 70%, 80%, 90%, 95%, 96%, 97%, 98%, 99%, or 100%. In other specific embodiments, given a particular configuration, the liquid flow to, through and/or around other reagent dot or other sets of reagent dots can be determined. Some or all of these variables can then be adjusted so that the liquid flow to, through and/or around other reagent dot or other sets of reagent dots be increased by at least 10%, and preferably by at least 20%, 30%, 40%, 50%, 60%, 70%, 80%, 90%, 95%, 96%, 97%, 98%, 99%, or 100%. In other embodiments, some or all of these variables can then be adjusted so that the liquid flow to, through and/or around other reagent dot or other sets of reagent dots be increased by 1 fold, 2 folds, 3 folds, 4 folds, 5 folds 6 folds, 7 folds, 8 folds, 9 folds, 10 folds, or more.

The test device can comprise any suitable number of reagent dots. In one example, the test device comprises two reagent dots. In another example, the test device comprises more than two reagent dots, such as at least 3, 4, 5, 6, 7, 8, 9, 10, 50, 100, 500, 1,000, 5,000, 10,000 or more reagent dots.

Any suitable number, portion or all of the reagent dots in the test device can be sufficiently spaced apart from each other. For example, at least a quarter, a third, half or all reagent dots do not overlap and are sufficiently spaced apart from each other so that when the liquid flows laterally along the matrix, flow of the liquid to, through and/or around one of the reagent dots does not substantially affect flow of the liquid to, through and/or around the other reagent dots.

The predetermined pattern formed at the reagent dots can take any form, shape and/or pattern. For example, the predetermined pattern can be a line, multiple lines, a symbol, a geometric shape and an alpha-numeric shape, a regular shape, or an irregular shape, or a combination thereof. The exemplary regular shape can be a line, a circle, a rod, a square, a triangle, and a rectangle. The exemplary alpha-numeric shape can be a letter, a word, a number or a combination thereof.

When the predetermined pattern is in the form of a line or multiple lines, the line(s) can be at any suitable orientation or position relative to the liquid flow direction. In one example, the line(s) is substantially parallel to the liquid flow direction. In another example, the line(s) is substantially perpendicular to the liquid flow direction. In still another example, the predetermined pattern is in the form of multiple lines. The multiple lines can comprise at least a line that is substantially parallel to the liquid flow direction and at least a line that is substantially perpendicular to the liquid flow direction. In some embodiments, at least a quarter, a third, half of the lines are substantially parallel to the liquid flow direction. In other embodiments, at least a quarter, a third, half of the lines are substantially perpendicular to the liquid flow direction.

The test device can be used to detect a single analyte or target or multiple analytes or targets in a liquid. In one example, the plurality of reagent dots in the test device comprises different reagents and the test device is used to detect multiple analytes or targets in a liquid. In another example, the plurality of reagent dots in the test device comprises the same reagent and the test device is used to detect the amount of a single analyte or target in a liquid.

The reagent dots in the test device can comprise any suitable amount of the reagent(s). In one example, the plurality of reagent dot comprises the same amount of the reagent(s). In another example, the plurality of reagent dots comprises the different amounts of the reagent(s).

The reagent dots in the test device can have any suitable size(s). In one example, at least one of the reagent dots has a diameter of about 0.1-1 um, 1-10 um, 10-50 um, 51-100 um, 101-200 um, 201-300 um, 301-400 um, 401-500 um and 501-1000 um. In another example, at least a quarter, a third, half or all reagent dots have a diameter of about 0.1-1 um, 1-10 um, 10-50 um, 51-100 um, 101-200 um, 201-300 um, 301-400 um, 401-500 um or 501-1000 um. In still another example, at least one of the reagent dots has a diameter or surface area that is about 10%, 5%, 1%, 0.5%, 0.1%, 0.05%, 0.01%, 0.001% or smaller diameter or surface area of the length, width or surface area of the matrix calculated by the width and length of the membrane. In yet another example, at least a quarter, a third, half or all reagent dots have a diameter or surface area that is about 10%, 5%, 1%, 0.5%, 0.1%, 0.05%, 0.01%, 0.001% or smaller diameter or surface area of the length, width or surface of the matrix.

Any suitable drop volumes can be used to make spots with any suitable or desirable sizes. In exemplary embodiments, the range of drop volumes used to create the range of spot sizes on the flow membrane can be in the range of about 30-200 pL, 201-500 pL, 501 pL-1.001 nL, 1.001 nL to 5.0 nL, 5.1-25 nL, 21.1-100 nL, or 100.1-500 nL. Shown in the below Table 1 is both spherical and hemispherical diameter of various drop sizes in the above drop range.

TABLE 1

| Drop Volume | Sphere Diameter (um) | Hemisphere Size (um) |
|---|---|---|
| 1 pL | 12.4 | 15.3 |
| 10 | 26.7 | 33.8 |
| 100 | 58 | 72 |
| 500 | 98 | 124 |
| 1 nL | 124 | 156 |
| 2.08 | 158 | 199 |
| 5 | 212 | 268 |
| 10 | 266 | 337 |
| 20 | 336 | 423 |
| 50 | 457 | 577 |
| 100 | 575 | 725 |
| 500 | 982 | 1243 |

The actual developed spot size of a reagent drop on the membrane can be larger, e.g., about 10-25% larger, than the hemispherical drop diameter. The sphere and hemispherical size of different drop volumes with the range described above is shown in the above Table 1.

The meaning of a "diameter" is often determined by the shape of the dot. For example, if the dot is a circle, the diameter of a circle is any straight line segment that passes through the center of the circle and whose endpoints are on the circle. The length of a diameter is also called the diameter. For a convex shape in the plane, the diameter is defined to be the largest distance that can be formed between two opposite parallel lines tangent to its boundary. The use of "diameter" does not limit the dot shape to be a circle or other regular shape. In some specific embodiments, when a dot has an irregular shape, a "diameter" can be measured as a parameter that indicates the length or width of the dot, e.g., measured as the largest distance between two points on the dot.

The reagent dots in the test device can have the same or different size(s) or diameter(s). In one example, at least a quarter, a third, half or all reagent dots have substantially the same size or diameter. In another example, at least a quarter, a third, half or all reagent dots have substantially different sizes or diameters.

The reagent dots in the test device can have any suitable shapes, e.g., any suitable regular or irregular shape. In one example, at least one of the reagent dots has a shape that is a line, a circle, a rod, a square, a triangle, a rectangle or an irregular shape. In another example, at least a quarter, a third, half or all reagent dots have a shape that is a line, a circle, a rod, a square, a triangle, a rectangle or an irregular shape. The reagent dots in the test device can have the same or different shape(s). In one example, at least a quarter, a third, half or all reagent dots have the same shape. In another example, at least a quarter, a third, half or all reagent dots have different shapes.

The reagent dots can have any suitable space(s) or distance(s) between or among the dots. In one example, the distance between or among the reagent dots is about 1-10 um, 10-50 um, 51-100 um, 101-200 um, 201-300 um, 301-400, 401-500, or 501-600 um. The space(s) or distance(s) between or among the reagent dots can be the same or different. In one example, the space or distance between at least a quarter, a third, half or all reagent dots is substantially the same. In another example, the space or distances between at least a quarter, a third, half or all reagent dots are different. Such space or distance can be measured by any suitable means. In some specific embodiments, the space or distance between or among reagent dots is measured as the space or distance between or among the edges of the reagent dots or adjacent reagent dots, e.g., distance between or among the edges of dots which defines the low resistance flow path of reagents. In other specific embodiments, the space or distance between or among reagent dots is measured as the space or distance between or among the centers or effective centers of the reagent dots or adjacent reagent dots.

The reagent dots can be located on any suitable places or side(s) of the matrix. In one example, the test device comprises a single layer of the plurality of reagent dot. In another example, the test device comprises multiple layers, e.g., 2, 3, 4, 5, 6, 7, 8, 9, 10 or more layers, of the plurality of reagent dots. In still another example, the test device comprises at least a layer of the plurality of reagent dots on one side of the matrix. In yet another example, the test device comprises at least a layer of the plurality of reagent dots on both sides of the matrix.

The signal(s) at the reagent dots can be generated by any suitable reactions, such as chemical, biochemical, electrochemical, and/or binding reactions involving the analyte, the target, the reagents located at the reagent dots, reagents added to the liquid sample and/or other liquid(s), and/or other reagents dried on the test device before use and that are transported by the liquid sample or other liquids to the reagent dots.

In some embodiments, the signal(s) at the reagent dots are generated based on binding reactions involving the analyte or target, the reagents located at the reagent dots, reagents added to the liquid sample and/or other liquid(s), and/or other reagents dried on the test device before use and that are transported by the liquid sample or other liquids to the reagent dots. In one example, at least one of the reagent dots comprises a reagent that is capable of binding to an analyte or a target, or another binding reagent that is capable of binding to an analyte or a target. Preferably, the reagent is capable of specifically binding to an analyte, a target, or another binding reagent that is capable of binding to an analyte or a target. Also preferably, the reagent avoids binding to interfering moiety or moieties in the testing sample or liquid. In another example, at least a quarter, a third, half or all reagent dots comprise a reagent that is capable of binding to an analyte, a target, or another binding reagent that is capable of binding to an analyte or a target. Preferably, the reagents are capable of specifically binding to an analyte, a target, or another binding reagent that is capable of binding to an analyte or a target.

The reagents located at the reagent dots can be any suitable substances. For example, the reagents can be inorganic molecules, organic molecules or complexes thereof. Exemplary inorganic molecules can be ions such as sodium, potassium, magnesium, calcium, chlorine, iron, copper, zinc, manganese, cobalt, iodine, molybdenum, vanadium, nickel, chromium, fluorine, silicon, tin, boron or arsenic ions. Exemplary organic molecules can be an amino acid, a peptide, a protein, e.g., an antibody or receptor, a nucleoside, a nucleotide, an oligonucleotide, a nucleic acid, e.g., DNA or RNA, a vitamin, a monosaccharide, an oligosaccharide, a carbohydrate, a lipid and a complex thereof.

Exemplary amino acids can be a D- or a L-amino-acid. Exemplary amino acids can also be any building blocks of naturally occurring peptides and proteins including Ala (A), Arg (R), Asn (N), Asp (D), Cys (C), Gln (Q), Glu (E), Gly (G), His (H), Ile (I), Leu (L), Lys (K), Met (M), Phe (F), Pro (P) Ser (S), Thr (T), Trp (W), Tyr (Y) and Val (V).

Any suitable proteins or peptides can be used as the reagents on the test device. For example, enzymes, transport proteins such as ion channels and pumps, nutrient or storage proteins, contractile or motile proteins such as actins and myosins, structural proteins, defense protein or regulatory proteins such as antibodies, hormones and growth factors can be used. Proteineous or peptidic antigens can also be used.

Any suitable nucleic acids, including single-, double and triple-stranded nucleic acids, can be used as the reagents on the test device. Examples of such nucleic acids include DNA, such as A-, B- or Z-form DNA, and RNA such as mRNA, tRNA and rRNA.

Any suitable nucleosides can be can be used as the reagents on the test device. Examples of such nucleosides include adenosine, guanosine, cytidine, thymidine and uridine. Any nucleotides can be used as the reagents on the test device. Examples of such nucleotides include AMP, GMP, CMP, UMP, ADP, GDP, CDP, UDP, ATP, GTP, CTP, UTP, dAMP, dGMP, dCMP, dTMP, dADP, dGDP, dCDP, dTDP, dATP, dGTP, dCTP and dTTP.

Any suitable vitamins can be used as the reagents on the test device. For example, water-soluble vitamins such as thiamine, riboflavin, nicotinic acid, pantothenic acid, pyridoxine, biotin, folate, vitamin $B_{12}$ and ascorbic acid can be used. Similarly, fat-soluble vitamins such as vitamin A, vitamin D, vitamin E, and vitamin K can be used.

Any suitable monosaccharides, whether D- or L-monosaccharides and whether aldoses or ketoses, can be used as the reagents on the test device. Examples of monosaccharides include triose such as glyceraldehyde, tetroses such as erythrose and threose, pentoses such as ribose, arabinose, xylose, lyxose and ribulose, hexoses such as allose, altrose, glucose, mannose, gulose, idose, galactose, talose and fructose and heptose such as sedoheptulose.

Any suitable lipids can be used as the reagents on the test device. Examples of lipids include triacylglycerols such as tristearin, tripalmitin and triolein, waxes, phosphoglycerides such as phosphatidylethanolamine, phosphatidylcholine, phosphatidylserine, phosphatidylinositol and cardiolipin, sphingolipids such as sphingomyelin, cerebrosides and gangliosides, sterols such as cholesterol and stigmasterol and sterol fatty acid esters. The fatty acids can be saturated fatty acids such as lauric acid, myristic acid, palmitic acid, stearic acid, arachidic acid and lignoceric acid, or can be unsaturated fatty acids such as palmitoleic acid, oleic acid, linoleic acid, linolenic acid and arachidonic acid.

In one specific embodiment, the analyte or target to be detected comprises or is an antigen, the binding reagent on the test device comprises or is an antibody. Preferably, the antibody specifically binds to the analyte or target. In one example, the test device is used in a sandwich assay format, in which a binding reagent, e.g., an antibody, is used as a reagent at the reagent dots, and another binding reagent having a detectable label is also used to form a labeled binding reagent-analyte-binding reagent or antibody sandwich at the reagent dots to generate readout signals. Alternatively, a binding reagent is used as a reagent at the reagent dots, and an antibody have a detectable label is also used to form a labeled antibody-analyte-binding reagent sandwich at the reagent dots to generate readout signals. In one example, the sandwich assay uses two antibodies, one as the capture reagent and the other as the labeled reagent.

The test device can also used in a competition assay format. In one example, a binding reagent, e.g., an antibody, is used as a capture reagent at the reagent dots. An analyte or analyte analog having a detectable label, either added in a liquid or previously dried on the test device and redissolved or resuspended by a liquid, will compete with an analyte or a target in a sample or liquid to bind to the capture reagent at the reagent dots. In another example, an analyte or analyte analog is used as a capture reagent at the reagent dots. A binding reagent, e.g., an antibody, having a detectable label, is either added in a liquid or previously dried on the test device and redissolved or resuspended by a liquid. An analyte in a sample will compete with the analyte, analyte analog or target at the reagent dots for binding to the binding reagent, e.g., an antibody, having a detectable label.

The matrix can have any suitable structure. In one example, the matrix can have a porous structure. The matrix can comprise any suitable material(s). For example, porous plastics material, such as polypropylene, polyethylene (preferably of very high molecular weight), polyvinylidene flouride, ethylene vinylacetate, acrylonitrile and polytetrafluoroethylene can be used. See e.g., U.S. Pat. No. 6,187,598. It can be advantageous to pre-treat the membrane with a surface-active agent during manufacture, as this can reduce any inherent hydrophobicity in the membrane and therefore enhance its ability to take up and deliver a moist liquid rapidly and efficiently. The matrix can also be made from paper or other cellulosic materials. In some embodiments, the matrix comprises or is made of nitrocellulose or glass fiber.

In another example, the matrix can have a non-porous structure, e.g., plastic solid surface. In some embodiments, the matrix can have other structures such as channels or other guided fluid pathways. In another example, the matrix comprises a plastic, a film of a matrix having a hydrophilic surface, or a material with a controlled contact angle with the sample liquid.

In yet another example, the test device can comprise at least one group of the reagent dots that form a circle around the sample or liquid application location, and the liquid moves radially to pass the group of the reagent dots. In yet another example, the test device can further comprise a flow through device portion.

The matrix can have any suitable form or shape. For example, the matrix can be in the form of a strip or a circle. The matrix can also have suitable number of elements. For example, the matrix can be made of a single element or can comprise multiple elements.

The test device can further comprise a liquid or sample application element upstream from and in fluid communication with the matrix. The liquid or sample application element can be made of any suitable materials, such as nitrocellulose, glass fiber, polypropylene, polyethylene (preferably of very high molecular weight), polyvinylidene flouride, ethylene vinylacetate, acrylonitrile or polytetrafluoro-ethylene. The matrix and the liquid or sample application element can comprise the same or different materials.

The test device can further comprise a liquid absorption element downstream from and in fluid communication with the matrix. The liquid absorption element can be made of any suitable materials, such as paper or cellulose materials.

In some embodiments, at least a portion of the matrix is supported by a solid backing. In other embodiments, half, more than half or all portion of the matrix is supported by a solid backing. The solid backing can be made of any suitable material, e.g., solid plastics. If the test device comprises electrode or other electrical elements, the solid backing should generally comprise non-conductive materials.

In some embodiments, a labeled reagent can be dried on the test device and the dried labeled reagent can be redissolved or resuspended by a liquid, e.g., a sample liquid and/or additional liquid, and transported laterally through the test device to generate readout, control and/or other signals. For example, a portion of the matrix, upstream from the at least two of the reagent dots, can comprise a dried, labeled reagent, the labeled reagent capable of being moved by a liquid sample and/or a further liquid to the at least two of the reagent dots and/or a control location to generate a detectable signal. The dried, labeled reagent can be located at any suitable places on the test device. In one example, the dried, labeled reagent is located downstream from a sample or liquid application place on the test device. In another example, the dried, labeled reagent is located upstream from a sample application or liquid place on the test device. The type of the labeled reagent can be determined based on the intended assay formats. For example, if the test device is to be used in a sandwich assay, the labeled reagent should be capable of binding, and preferably capable of specifically binding, to the analyte or a target, or another substance that binds to the analyte or the target. The same labeled reagent can also be used for certain competitive binding assays. For other types of the competitive binding assays, the labeled reagent should be an analyte or an analyte analog linked to a detectable label.

In some embodiments, the test device can further comprise, upstream from the at least two of the reagent dots, a conjugate element that comprises a dried, labeled reagent, the labeled reagent being capable of moved by a liquid sample and/or a further liquid to the at least two of the reagent dots and/or a control location to generate a detectable signal. The conjugate element can be located downstream from a liquid or sample application place on the test device. The conjugate element can also be located upstream from a liquid or sample application place on the test device. In some embodiments, the labeled reagent binds to an analyte or a target in the liquid sample. In other embodiments, the labeled reagent competes with an analyte or a target in the liquid sample for binding to a binding reagent for the analyte or target at the at least two of the reagent dots.

Any suitable label can be used. The label can be a soluble label, such as a colorimetric, radioactive, enzymatic, luminescent or fluorescent label. The label can also be a particle or particulate label, such as a particulate direct label, or a colored particle label. Exemplary particle or particulate labels include colloidal gold label, latex particle label, nanoparticle label and quantum dot label. Depending on the specific configurations, the labels such as colorimetric, radioactive, enzymatic, luminescent or fluorescent label, can be either a soluble label or a particle or particulate label.

In some embodiments, the labeled reagent is dried in the presence of a material that stabilizes the labeled reagent, facilitates solubilization or resuspension of the labeled reagent in a liquid, and/or facilitates mobility of the labeled reagent. Any suitable material can be used. For example, the material can be a protein, e.g., a meta-soluble protein, a peptide, a polysaccharide, a sugar, e.g., sucrose, a polymer, a gelatin or a detergent. See e.g., U.S. Pat. Nos. 5,120,643 and 6,187,598.

The present test devices can be used with any suitable liquid. In one example, a sample liquid alone is used to transport the analyte, the target and/or the labeled reagent to the at least two of the reagent dots. In another example, a developing liquid is used to transport the analyte, the target and/or the labeled reagent to the at least two of the reagent dots. In still another example, both sample liquid and a developing liquid is used to transport the analyte, the target and/or the labeled reagent to the at least two of the reagent dots.

In some embodiments, the test device can further comprise a housing that covers at least a portion of the test device, wherein the housing comprises a sample or liquid application port to allow sample or liquid application upstream from or to the at least two of the reagent dots and an optic opening around the at least two of the reagent dots to allow signal detection at the two of the reagent dots. The optic opening can be achieved in any suitable way. For example, the optic opening can simply be an open space. Alternatively, the optic opening can be a transparent cover.

In other embodiments, the housing can cover the entire test device. In still other embodiments, at least a portion of the sample receiving portion of the matrix or the sample application element is not covered by the housing and a sample or liquid is applied to the portion of the sample receiving portion of the matrix or the sample application element outside the housing and then transported to the at least two of the reagent dots. The housing can comprise any suitable material. For example, the housing can comprise a plastic material, a biodegradable material or a cellulosic material. In another example, the housing, whether in part or in its entirety, can comprise an opaque, translucent and/or transparent material.

In some embodiments, the present invention provides for a test device wherein the liquid or sample has moved laterally along the test device to generate detectable signal(s) at the at least two of the reagent dots.

C. Methods for Detecting an Analyte Using a Lateral Flow Device with Two Dimensional Features In another aspect, the present disclosure provides for a method for a method, which method comprises: a) contacting a liquid with the test device described in the above Section B, wherein the liquid is applied to a site of said test device upstream of said at least two reagent dots; b) transporting a labeled reagent to said at least two reagent dots; and c) assessing the presence, absence, amount and/or pattern of signal(s) generated by said labeled reagent at said at least two reagent dots to provide for flow control information, to function as an internal control and/or to provide for internal calibration information for said test device.

In an exemplary embodiment, the signal(s) at the reagent dots can be generated by binding reactions involving the analyte or target and the reagents located at the reagent dots, and a labeled reagent added to the liquid or dried on the test device before use and is transported by the liquid sample or other liquids to the reagent dots. For example, the method comprises a) contacting a liquid with the above test device, wherein the liquid is applied to a site of the test device upstream of the at least two of the reagent dots; b) transporting an analyte or target, if present in the liquid, and a labeled reagent to the at least two of the reagent dots; and c) assessing the presence, absence, amount and/or pattern of signal(s) at the at least two of the reagent dots, e.g., signal(s) generated by the labeled reagent at the at least two of the reagent dots, to provide for flow control information, to function as an internal control and/or to provide for internal calibration information for said test device, and/or to determine the presence, absence and/or amount of the analyte in the liquid sample.

In some embodiments, the liquid and the labeled reagent are premixed to form a mixture and the mixture is applied to the test device. For example, the labeled reagent can be provided or stored in a liquid and then can be premixed with a liquid to form a mixture and the mixture is applied to the test device. In another example, the labeled reagent can be dried in a location or container not in fluid communication with the test device, e.g., in a test tube or well such as a microtiter plate well. In use, the sample liquid can be added to the container, e.g., the test tube or well, to form the mixture and the mixture can then be applied to the test device.

In other embodiments, the test device comprises a dried labeled reagent before use and the dried labeled reagent is solubilized or resuspended, and transported to the at least two of the reagent dots by the liquid sample and/or other liquid. The dried labeled reagent can be located at any suitable location on the test device. For example, the dried labeled reagent can be located downstream from the sample or liquid application site, and the dried labeled reagent can be solubilized or resuspended, and transported to the at least two of the reagent dots by the liquid sample and/or other liquid. In another example, the dried labeled reagent can be located upstream from the sample or liquid application site, and the dried labeled reagent can be solubilized or resuspended, and transported to the at least two of the reagent dots by another liquid.

In some embodiments, the labeled reagent is solubilized or resuspended, and transported to the at least two of the reagent dots by the liquid sample alone. In other embodiments, the analyte, target and/or labeled reagent is solubilized or resuspended, and transported to the at least two of the reagent dots by another liquid. In still other embodiments, the analyte, target and/or labeled reagent is solubilized or resuspended, and transported to the at least two of the reagent dots by both the sample liquid and another liquid, e.g., a developing liquid.

In some embodiments, the detectable signals are formed at the at least two reagent dots to provide for or to function as at least two of the following: 1) to provide for flow control information; 2) to function as an internal control; and 3) to provide for internal calibration information for the test device. In other embodiments, the detectable signals are formed to provide for flow control information, to function as an internal control and to provide for internal calibration information for the test device.

In some embodiments, the present methods further comprise detecting an analyte in a liquid sample. The present methods can also incorporate the methods disclosed and/or claimed in U.S. provisional application Ser. No. 61/461,499, filed Jan. 18, 2011, U.S. patent application Ser. No. 13/343,681, filed Jan. 4, 2012, and international patent application No. PCT/US2012/021586, filed Jan. 17, 2012, to provide for flow control information, an internal control and/or internal calibration information for the test device, and to indicate presence, absence and/or amount of an analyte in a liquid sample.

The present test devices can be used in connection with and/or to detect an analyte in any suitable sample liquid. In some embodiments, the liquid sample can be body fluid sample, such as a whole blood, a serum, a plasma, a urine sample or an oral fluid. Such body fluid sample can be sued directly or can be processed, e.g., enriched, purified, or diluted, before use. In other embodiments, the liquid sample can be a liquid extract, suspension or solution derived from a solid or semi-solid biological material such as a phage, a virus, a bacterial cell, an eukaryotic cell, a fugal cell, a mammalian cell, a cultured cell, a cellular or subcellular structure, cell aggregates, tissue or organs. In specific embodiments, the sample liquid is obtained or derived from a mammalian or human source. In still other embodiments, the liquid sample is a sample derived from a biological, a forensics, a food, a biowarfare, or an environmental source. In other embodiments, the sample liquid is a clinical sample, e.g., a human or animal clinical sample. In still other embodiments, the sample liquid is a man-made sample, e.g., a standard sample for quality control or calibration purposes.

The present test devices can be used to detect the presence, absence and/or amount of an analyte in any suitable sample liquid. In some embodiments, the present test devices are used to detect the presence or absence of an analyte in any suitable sample liquid, i.e., to provide a yes or no answer. In other embodiments, the present test devices are used to quantify or semi-quantify the amount of an analyte in a liquid sample.

The present test devices can be used to detect the presence, absence and/or amount of a single analyte in any suitable sample liquid. Alternatively, the present test devices can be used to detect the presence, absence and/or amount of multiple analytes in a liquid sample. In still other embodiments, the present test devices can be used to quantify or semi-quantify the amounts of the multiple analytes in the liquid sample.

The present test devices can be used to detect the presence, absence and/or amount of any suitable analyte in a sample liquid. Exemplary analytes include inorganic molecules, organic molecules or complexes thereof. Exemplary inorganic molecules can be ions such as sodium, potassium, magnesium, calcium, chlorine, iron, copper, zinc, manganese, cobalt, iodine, molybdenum, vanadium, nickel, chromium, fluorine, silicon, tin, boron or arsenic ions. Exemplary organic molecules can be an amino acid, a peptide, a protein, a nucleoside, a nucleotide, an oligonucleotide, a nucleic acid, e.g., a DNA or RNA molecule or a hybrid thereof, a vitamin, a monosaccharide, an oligosaccharide, a carbohydrate, a lipid and a complex thereof. In some embodiments, the analyte is a cell, a virus or a molecule. In other embodiments, the analyte is hCG, hLH, hFSH, hTSH, a disease or disorder marker, e.g., a cardiac biomarker, an antigen of an infectious organism, an antibody to an infectious organism, etc.

The present methods can be used for any suitable purpose. For example, present methods can be used for clinical diagnosis, prognosis, risk assessment and prediction, stratification and treatment monitoring and adjustment. In another example, present methods can be used for various research purposes, such as basic research, drug candidate screening, animal studies, and clinical trials. In still another example, present methods can be used in tests for standard setting, quality control, illegal drug screening, food safety, environmental safety, industrial safety, pollution, detection of biowarfare agents, screening for drugs or pharmaceuticals, and monitoring the quality of manufacturing using bioreactors looking for unwanted molecules, etc. The present tests devices and methods can be used in any suitable settings, such as tests in the labs, clinics, hospitals, physician's offices, homes, natural environments, battle fields and first responder environments, e.g., environments for fire, paramedic, police actions.

D. Exemplary Embodiments

In some embodiments, the present disclosure relates to methods and devices used in lateral flow testing of a range of analytes by means of the creation of arrays of reagent dots ("pixels") in or on a substrate that is designed to transport fluids within a rapid test device and across the pixel array, and to methods for assembling those pixel arrays in orientations that generate signals indicative of results of the test in a variety of symbols and formats which can be interpreted by the user. The dispensing of the capture reagent is performed in a highly controlled manner with the intent of allowing the migrating analyte and conjugate in the system to react with each dispensed feature ("pixel") without causing perturbation of the flow pattern in the system that prevents interaction with any subsequent features.

The ability to generate features in the flow field allows for the generation of control features in the assay that in turn allow for a number of advanced functionalities, including flow controls, internal positive and negative controls for assays, and internal calibration curves.

Flow controls: Features in the flow field that allow internal calibration within the strip for any perturbation in results caused by variability in flowrate or flow pattern laterally across the surface, and also along the length of the flow field, where flowrate decreases inversely and non-linearly with distance from origin. Such changes in flow rate can have effects on the kinetics of assays and may be important where quantification is required.

These control features may be set up in the field of flow in a number of orientations. They may contain dots or other feature types placed perpendicular and/or parallel to the direction of flow, or randomly within the flow field.

Internal positive and negative controls for assays: The lateral flow system is typically designed with a single internal control line, which may be analyte dependent or independent. This control line is used primarily as a flow control, indicating that the strip has mechanically run appropriately and indicating that the result read on the test line can be considered valid. The analyte dependent control line serves this same function, but in addition serves to identify that the sample used contained some detectable element expected in the sample matrix that should be applied to the device. For example, an anti-alpha amylase might be used to identify that a true saliva sample has been applied to the device. While these represent functional controls, there are several other control features that could be usefully applied in lateral flow, which are commonly applied in other analytical methods, but which the standard lateral flow design does not allow for.

These can be created using the pixilation method embodied in U.S. provisional application Ser. No. 61/461,499, filed Jan. 18, 2011, U.S. patent application Ser. No. 13/343,681, filed Jan. 4, 2012, and international patent application No. PCT/US2012/021586, filed Jan. 17, 2012. These features include internal controls for cross reactivity or interfering substances, internal positive controls of constant or varying intensity at various locations in the field, and internal true negatives for establishment of baseline. These features may be set up as dots within the flow field in repeated or random locations, or may be lines or other feature types.

Internal Calibration Curves: A major issue in the lateral flow system is the relatively complex system of calibration required for any degree of quantification to be attained. We will consider primarily electronic reader-interpreted assay systems, however the same principles will apply to an assay that is visually interpreted by an operator. The calibration system can contain several elements. One element is internal reader calibration of optics and illumination.

Another element is related to wet calibrators, standards that are run at the point of operation of the device to ensure that the system is in calibration. In the case of lateral flow, these are generally samples of known performance or standard solutions in buffer that are run on actual test strips and evaluated in the reader.

Still another element is related to calibration standards: Unchanging calibrants, such as a grey scale or a solid white chip against which a reader calibrates its operation. These may be external, evaluated in the reader on a periodic basis, or they may be internal to the reader, evaluated on start up or before each run. For fluorescent assays, this type of calibration represents a challenge, as fluorophores tend to degrade due to photobleaching, meaning that the calibration standards change over time and must be replaced regularly, or another solution must be found. Reader suppliers have approached this differently; for example Qiagen Lake Constance has developed a system of containing rare earth elements in polymer coatings to prevent photobleaching. LRE is developing a system that uses a visual calibration method and referencing that to the operation of the fluorophore via a proprietary algorithm.

Yet another element is related to programmed calibration. Each batch of lateral flow strips will typically have a standard curve generated for it, against which it will be measured. The number of parameters applied to that standard curve and the type of curve fitting used will vary from test to test. The information for each batch of strips must be communicated to the reader before the results from the test can be analyzed. That communication is performed in a variety of ways, including the use of bar codes and RFID tags on tests or packaging, that are scanned by the reader, or the manual input of calibration data into the reader before tests are run.

In some embodiments, the present disclosure allows for the generation of a variety of internal calibration features within the flow field of the lateral flow system. These include internal calibration curve using analyte dependent binding features, internal calibration curve using analyte independent binding features and internal calibration spots or features for reader calibration.

Internal calibration curve using analyte dependent binding features: This format can be envisaged as a series of spots, lines or more complex features in the flow field of a specific calibration strip. Rather than running multiple calibration strips using wet calibrators, or creating external calibration strips with pre-developed signals of fixed strength, it is possible to develop a single test strip with multiple calibration features on board to account for flow effects and degradation of conjugates, while developing an analyte dependent calibration curve. A single strip could thereby be used to calibrate the reader system removing the need to test multiple strips and the difficult task of generating an internal, unchanging hard calibrant. This would be particularly useful for fluorescent or chemiluminescent systems, where creation of such unchanging standards is difficult.

Internal calibration curve using analyte independent binding features: This can be envisaged as a series of spots, lines or more complex features in the flow field of the actual test strip being used for evaluation of an unknown sample. A calibration curve using the actual conjugated signal molecule and an analyte independent binding reagent, which could be either the analyte itself bound to the reaction matrix or an alternative reagent, would be generated in the flow field. This may be combined with a series of other control features, including non-specific binding controls and flow rate controls, as described previously.

Internal calibration spots or features for reader calibration: These features may be included in the device with the specific aim of aiding in reader calibration. They may be envisaged as spots in the flow field that have been impregnated with a specific binding reagent that is designed to generate signals of specific strengths relative to one another or absolute signal strengths of differing levels. The analysis of the signal strengths generated at these features may be combined with the signal strengths generated by internal flow controls to compensate for any changes in kinetics caused by flowrate down or across the strip. Analysis of the two sets of control features will allow for the removal of mechanical effects and of label related degradation, thereby allowing for the calibration of reader performance on the actual test being run.

The present invention is further illustrated by the following exemplary embodiments:

1. A test device, which device comprises a plurality of reagent dots on a matrix, wherein at least two of said reagent dots do not overlap and are sufficiently spaced apart from each other so that when a liquid flows laterally along said matrix, flow of said liquid to, through and/or around one of said two reagent dots does not substantially affect flow of said liquid sample to, through and/or around said other reagent dot, each of said two reagent dots is neither a reagent line across the entire width of said matrix in a direction perpendicular to the direction of said liquid flow nor a complete circle of a reagent line circulating the center or sample or liquid application site of said test device, and after a liquid flows laterally along said test device and passes said at least two reagent dots, detectable signals are formed at said at least two reagent dots to provide for flow control information, to function as an internal control and/or to provide for internal calibration information for said test device.

2. The test device of embodiment 1, wherein the detectable signals are formed at the at least two reagent dots to provide for flow control information for the test device.

3. The test device of embodiment 2, wherein the flow control information allows internal calibration within the test device for perturbation in test results caused by variability in flow rate or flow pattern laterally across the surface and/or along the length of the flow field.

4. The test device of embodiment 2 or 3, which test device further comprises a detection site to indicate presence, absence and/or amount of an analyte in a liquid sample.

5. The test device of embodiment 4, wherein the formation of the detectable signals at the at least two reagent dots is independent from the presence, absence and/or amount of the analyte in a liquid sample.

6. The test device of embodiment 5, wherein each of the at least two reagent dots comprises a reagent that binds to a labeled binding reagent for the analyte, preferably a labeled specific binding reagent for the analyte.

7. The test device of embodiment 6, wherein the reagent at each of the at least two reagent dots comprises an analyte or analyte analog.

8. The test device of embodiment 4, wherein the formation of the detectable signals at the at least two reagent dots depends on the presence and/or amount of the analyte or a non-analyte substance in a liquid sample.

9. The test device of embodiment 8, wherein each of the at least two reagent dots comprises a reagent that binds to the analyte, preferably a reagent that specifically binds to the analyte.

10. The test device of embodiment 8, wherein each of the at least two reagent dots comprises a reagent that binds to the non-analyte substance. Preferably, a reagent that specifically binds to the non-analyte substance.

11. The test device of any of the embodiments 1-10, wherein the at least two reagent dots form a line that is substantially parallel to the liquid flow direction, a line that is substantially perpendicular to the liquid flow direction and/or a line that is at a predetermined angle relative to the liquid flow direction.

12. The test device of embodiment 11, wherein each of the at least two reagent dots comprises the same reagent.

13. The test device of embodiment 12, wherein each of the at least two reagent dots comprises the same amount of the reagent.

14. The test device of embodiment 12, wherein the at least two reagent dots comprise different amounts of the reagent.

15. The test device of any of the embodiments 1-4, wherein the detectable signal is formed at one or more of the at least two reagent dots to function as an internal control for the test device.

16. The test device of embodiment 15, wherein the detectable signal is formed at a single reagent dot to function as an internal control for the test device.

17. The test device of embodiment 15, wherein the detectable signals are formed at a plurality of reagent dots to function as an internal control for the test device.

18. The test device of any of the embodiments 15-17, wherein the internal control is an internal control for cross reactivity or an interfering substance, an internal positive control, and/or an internal negative control.

19. The test device of embodiment 18, wherein the internal control is an internal control for cross reactivity or an interfering substance.

20. The test device of embodiment 19, wherein the reagent dot that functions as the internal control for cross reactivity or an interfering substance comprises a reagent for binding to an analyte analog or an interfering substance that is known or likely to be present in a testing sample, preferably a reagent for specifically binding to an analyte analog or an interfering substance.

21. The test device of embodiment 20, wherein the detectable signal forms a predetermined pattern indicating the presence and/or amount of cross reactivity or an interfering substance in a testing sample.

22. The test device of any of the embodiments 19-21, wherein a plurality of the reagent dots function as the internal control for cross reactivity or an interfering substance.

23. The test device of embodiment 18, wherein the internal control is an internal positive control.

24. The test device of embodiment 23, wherein the formation of the detectable signal(s) at the reagent dot(s) depends on the presence and/or amount of the analyte and/or a non-analyte substance in a liquid sample.

25. The test device of embodiment 24, wherein the reagent dot that functions as the internal positive control comprises a reagent for binding to an analyte or a non-analyte substance, preferably a reagent for specific binding to an analyte or a non-analyte substance.

26. The test device of embodiment 25, wherein the detectable signal forms a predetermined pattern indicating the analyte or a non-analyte substance in a testing sample.

27. The test device of any of the embodiments 23-26, wherein a plurality of the reagent dots function as the internal positive controls.

28. The test device of embodiment 27, wherein the signals at the plurality of the reagent dots comprise constant intensity or varying intensities at various locations.

29. The test device of embodiment 18, wherein the internal control is an internal negative control.

30. The test device of embodiment 29, wherein the reagent dot is treated as the same for a test site except that a regent for binding to an analyte is not applied to the reagent dot to function as an internal negative control.

31. The test device of embodiment 29 or 30, wherein a plurality of the reagent dots functions as the internal negative controls.

32. The test device of any of the embodiments 1-4, wherein the detectable signals are formed at the at least two reagent dots to provide internal calibration information for the test device.

33. The test device of embodiment 32, wherein the formation of the detectable signals at the at least two reagent dots is independent from the presence, absence and/or amount of the analyte in a liquid sample.

34. The test device of embodiment 33, wherein each of the at least two reagent dots comprises a reagent that binds to a labeled binding reagent for the analyte, preferably a reagent that specifically binds to a labeled binding reagent for the analyte.

35. The test device of embodiment 34, wherein the reagent at each of the at least two reagent dots comprises an analyte or analyte analog.

36. The test device of any of the embodiments 32-35, wherein the detectable signals are formed at the at least two reagent dots to provide for internal calibration information for the desired analyte testing range.

37. The test device of any of the embodiments 32-36, wherein the at least two reagent dots form a line that is substantially parallel to the liquid flow direction, a line that is substantially perpendicular to the liquid flow direction and/or a line that is at a predetermined angle relative to the liquid flow direction.

38. The test device of embodiment 37, wherein the detectable signals at the reagent dots form a gradient of signal strength in a direction of the line formed by the reagent dots.

39. The test device of any of the embodiments 32-38, wherein the test device does not comprise a detection site to indicate presence, absence and/or amount of an analyte in a liquid sample and the detectable signals are formed at the at least two reagent dots to provide for internal calibration information for the test device.

40. The test device of embodiment 39, wherein the formation of the detectable signals at the at least two reagent dots depends on the presence and/or amount of the analyte in a calibration liquid.

41. The test device of embodiment 40, wherein each of the at least two reagent dots comprises a reagent that binds to the analyte, preferably a reagent that specifically binds to the analyte.

42. The test device of any of the embodiments 39-41, wherein the detectable signals are formed at the least two reagent dots to provide for internal calibration information for the desired analyte testing ranging.

43. The test device of any of the embodiments 39-42, wherein the at least two reagent dots form a line that is substantially parallel to the liquid flow direction, a line that is substantially perpendicular to the liquid flow direction and/or a line that is at a predetermined angle relative to the liquid flow direction.

44. The test device of embodiment 43, wherein the detectable signals at the reagent dots form a gradient of signal strength in a direction of the line formed by the reagent dots.

45. The test device of embodiment 44, wherein each of the at least two reagent dots comprises a reagent that binds to the analyte, preferably a reagent that specifically binds to the analyte, and the amount of the reagent forms a gradient in a direction of the line for the reagent dots.

46. The test device of embodiment 43, wherein the detectable signal at the reagent dots is the same for a predetermined level of analyte in a calibration liquid.

47. The test device of any of the embodiments 1-3, wherein the test device does not comprise a detection site to indicate presence, absence and/or amount of an analyte in a liquid sample and the at least two reagent dots comprise a binding reagent that is adopted to generate signals of specific signal strengths relative to one another or absolute signal strengths of differing levels.

48. The test device of embodiment 47, wherein the at least two reagent dots form a line that is substantially parallel to the liquid flow direction, a line that is substantially perpendicular to the liquid flow direction and/or a line that is at a predetermined angle relative to the liquid flow direction.

49. The test device of any of the embodiments 1-48, wherein the detectable signals are formed at the at least two reagent dots to provide for or to function at least two of the following:
 1) to provide for flow control information;
 2) to function as an internal control; and
 3) to provide for internal calibration information for said test device.

50. The test device of any of the embodiments 1-48, wherein the detectable signals are formed to provide for flow control information, to function as an internal control and to provide for internal calibration information for the test device.

51. The test device of any of the embodiments 1-50, wherein the plurality of reagent dots comprises two reagent dots.

52. The test device of any of the embodiments 1-50, wherein the plurality of reagent dots comprises more than two reagent dots.

53. The test device of any of the embodiments 1-50, wherein the plurality of reagent dots comprises at least 10, 50, 100, 500, 1,000, 5,000, 10,000 or more reagent dots.

54. The test device of any of the embodiments 1-53, wherein at least a quarter, a third, half of or all the reagent dots do not overlap and are sufficiently spaced apart from each other so that when the liquid or liquid sample flows laterally along the matrix, flow of the liquid or liquid sample to, through and/or around one of the reagent dots does not substantially affect flow of the liquid or liquid sample to, through and/or around the other reagent dots.

55. The test device of any of the embodiments 1-54, wherein the detectable signals at the at least two reagent dots form a predetermined pattern.

56. The test device of embodiment 55, wherein the predetermined pattern is selected from the group consisting of a line, multiple lines, a symbol, a geometric shape and an alpha-numeric shape.

57. The test device of embodiment 56, wherein the alpha-numeric shape is a letter, a word, a number or a combination thereof.

58. The test device of any of the embodiments 1-57, wherein at least two reagent dots comprise the same amount of the reagent(s).

59. The test device of any of the embodiments 1-57, wherein at least two reagent dots comprise different amounts of the reagent(s).

60. The test device of any of the embodiments 1-59, wherein at least one of the reagent dots has a diameter of about 0.1-1 um, 1-10 um, 10-50 um, 51-100 um, 101-200 um, 201-300 um, 301-400 um, 401-500 um and 501-1000 um, or at least one of the reagent dots has a diameter or surface area that is about 10%, 5%, 1%, 0.5%, 0.1%, 0.05%, 0.01%, 0.001% or smaller diameter or surface area of the length, width or surface area of the matrix.

61. The test device of embodiment 60, wherein at least a quarter, a third, half of or all the reagent dots have a diameter of about 0.1-1 um, 1-10 um, 10-50 um, 51-100 um, 101-200 um, 201-300 um, 301-400 um, 401-500 um or 501-1000 um, or at least a quarter, a third, half of or all the reagent dots have a diameter or surface area that is about 10%, 5%, 1%, 0.5%, 0.1%, 0.05%, 0.01%, 0.001% or smaller diameter or surface area of the length, width or surface of the matrix.

62. The test device of embodiment 60, wherein at least a quarter, a third, half of or all the reagent dots have substantially the same size or diameter.

63. The test device of any of the embodiments 1-62, wherein at least one of the reagent dots has a shape selected from the group consisting of a line, a circle, a rod, a square, a triangle, a rectangle and an irregular shape.

64. The test device of embodiment 63, wherein at least a quarter, a third, half of or all the reagent dots have a shape selected from the group consisting of a line, a circle, a rod, a square, a triangle, a rectangle and an irregular shape.

65. The test device of embodiment 63, wherein at least a quarter, a third, half of or all the reagent dots have the same shape.

66. The test device of any of the embodiments 1-65, wherein the distance between edges of at least two of the reagent dots is about 1-10 um, 10-50 um, 51-100 um, 101-200 um, 201-300 um, 301-400, 401-500, or 501-600 um.

67. The test device of embodiment 66, wherein the distance between at least a quarter, a third, half of or all the reagent dots is substantially the same.

68. The test device of any of the embodiments 1-67, which comprises multiple layers of the plurality of reagent dots.

69. The test device of any of the embodiments 1-68, which comprises at least a layer of the plurality of reagent dots on both sides of the matrix.

70. The test device of any of the embodiments 1-69, wherein the reagents are inorganic molecules, organic molecules or complexes thereof.

71. The test device of embodiment 70, wherein the organic molecules are selected from the group consisting of an amino acid, a peptide, a protein, a nucleoside, a nucleotide, an oligonucleotide, a nucleic acid, a vitamin, a monosaccharide, an oligosaccharide, a carbohydrate, a lipid and a complex thereof.

72. The test device of embodiment 71, wherein the protein is an antigen or an antibody.

73. The test device of any of the embodiments 1-72, wherein the matrix has a porous structure.

74. The test device of embodiment 73, wherein the matrix comprises nitrocellulose, glass fiber, polypropylene, polyethylene (preferably of very high molecular weight), polyvinylidene flouride, ethylene vinylacetate, acrylonitrile and/ or polytetrafluoro-ethylene.

75. The test device of any of the embodiments 1-72, wherein the matrix has a non-porous structure.

76. The test device of embodiment 75, wherein the matrix comprises a plastics, a film of a matrix having a hydrophilic surface, or a material with a controlled contact angle with the sample liquid.

77. The test device of any of the embodiments 1-76, which further comprises a flow through device portion.

78. The test device of any of the embodiments 1-77, wherein the matrix is in the form a strip or a circle.

79. The test device of any of the embodiments 1-78, wherein the matrix is a single element or comprises multiple elements.

80. The test device of any of the embodiments 1-79, which further comprises a liquid or sample application element upstream from and in fluid communication with the matrix.

81. The test device of any of the embodiments 1-80, which further comprises a liquid absorption element downstream from and in fluid communication with the matrix.

82. The test device of any of the embodiments 1-81, wherein at least a portion of the matrix is supported by a solid backing.

83. The test device of any of the embodiments 1-82, wherein a portion of the matrix, upstream from the at least two of the reagent dots, comprises a dried, labeled reagent, the labeled reagent being capable of being moved by a liquid or liquid sample to the at least two of the reagent dots and/or a test site to generate a detectable signal.

84. The test device of embodiment 83, wherein the dried, labeled reagent is located downstream from a liquid or sample application place on the test device.

85. The test device of embodiment 83, wherein the dried, labeled reagent is located upstream from a liquid or sample application place on the test device.

86. The test device of any of the embodiments 1-85, which further comprises, upstream from the at least two of the reagent dots, a conjugate element that comprises a dried, labeled reagent, the labeled reagent being capable of moved by a liquid or liquid sample to the at least two of the reagent dots and/or a test site to generate a detectable signal.

87. The test device of embodiment 86, wherein the conjugate element is located downstream from a liquid or sample application place on the test device.

88. The test device of embodiment 86, wherein the conjugate element is located upstream from a liquid or sample application place on the test device.

89. The test device of any of the embodiments 86-88, wherein the labeled reagent binds to an analyte or a non-analyte substance in the liquid sample, preferably the labeled reagent specifically binds to an analyte or a non-analyte substance in the liquid sample.

90. The test device of any of the embodiments 86-89, wherein the label is a soluble label.

91. The test device of any of the embodiments 86-89, wherein the label is a particle label.

92. The test device of any of the embodiments 86-91, wherein the labeled reagent is dried in the presence of a material that: a) stabilizes the labeled reagent; b) facilitates solubilization or resuspension of the labeled reagent in a liquid; and/or c) facilitates mobility of the labeled reagent.

93. The test device of embodiment 92, wherein the material is selected from the group consisting of a protein, a peptide, a polysaccharide, a sugar, a polymer, a gelatin and a detergent.

94. The test device of any of the embodiments 86-93, wherein a sample liquid alone is used to transport the analyte and/or the labeled reagent to the at least two of the reagent dots.

95. The test device of any of the embodiments 86-93, wherein a developing liquid is used to transport the analyte and/or the labeled reagent to the at least two of the reagent dots.

96. The test device of any of the embodiments 1-95, which further comprises a housing that covers at least a portion of the test device, wherein the housing comprises a sample or liquid application port to allow sample or liquid application upstream from or to the at least two of the reagent dots and an optic opening around the at least two of the reagent dots to allow signal detection at the two of the reagent dots.

97. The test device of embodiment 96, wherein the housing covers the entire test device.

98. The test device of embodiment 96, wherein at least a portion of the sample receiving portion of the matrix or the sample or liquid application element is not covered by the housing and a sample or liquid is applied to the portion of the sample or liquid receiving portion of the matrix or the sample or liquid application element outside the housing and then transported to the at least two of the reagent dots.

99. The test device of any of the embodiments 96-98, wherein the housing comprises a plastic material, a biodegradable material or a cellulosic material.

100. The test device of any of the embodiments 1-99, wherein the liquid or sample has moved laterally along the test device to generate detectable signal(s) at the at least two of the reagent dots.

101. A method, which method comprises:
a) contacting a liquid with the test device of any of the embodiments 1-100, wherein the liquid is applied to a site of said test device upstream of said at least two reagent dots;
b) transporting a labeled reagent to said at least two reagent dots; and
c) assessing the presence, absence, amount and/or pattern of signal(s) generated by said labeled reagent at said at least two reagent dots to provide for flow control information, to function as an internal control and/or to provide for internal calibration information for said test device.

102. The method of embodiment 101, wherein the liquid and the labeled reagent are premixed to form a mixture and the mixture is applied to the test device.

103. The method of embodiment 101, wherein the test device comprises a dried labeled reagent before use and the dried labeled reagent is solubilized or resuspended, and transported to the at least two reagent dots by the liquid.

104. The method of embodiment 103, wherein the dried labeled reagent is located downstream from the sample or liquid application site, and the dried labeled reagent is solubilized or resuspended, and transported to the at least two of the reagent dots by the liquid.

105. The method of embodiment 103, wherein the dried labeled reagent is located upstream from the sample or liquid application site, and the dried labeled reagent is solubilized or resuspended, and transported to the at least two reagent dots by another liquid.

106. The method of any of the embodiments 103-105, wherein the liquid is a body fluid sample.

107. The method of embodiment 106, wherein the body fluid sample is selected from the group consisting of a whole blood, a serum, a plasma and a urine sample.

108. The method of any of the embodiments 101-107, wherein the detectable signals are formed at the at least two reagent dots to provide for or to function as at least two of the following:
1) to provide for flow control information;
2) to function as an internal control; and
3) to provide for internal calibration information for the test device.

109. The method of any of the embodiments 101-107, wherein the detectable signals are formed to provide for flow control information, to function as an internal control and to provide for internal calibration information for the test device.

110. The method of any of the embodiments 101-109, which further comprises detecting an analyte in a liquid sample.

The ordinarily skilled artisan can appreciate that the present invention can incorporate any number of the preferred features described above.

Further features and advantages of the present invention will become apparent to those of skill in the art in view of the detailed description of specific embodiments, when considered together with the attached drawings and claims.

The above examples are included for illustrative purposes only and are not intended to limit the scope of the invention. Many variations to those described above are possible. Since modifications and variations to the examples described above will be apparent to those of skill in this art, it is intended that this invention be limited only by the scope of the appended claims.

Citation of the above publications or documents is not intended as an admission that any of the foregoing is pertinent prior art, nor does it constitute any admission as to the contents or date of these publications or documents.

What is claimed is:

1. A test device, which device comprises a plurality of reagent dots on a matrix, wherein at least two of said reagent dots do not overlap and are sufficiently spaced apart from each other so that when a liquid flows laterally along said matrix, flow of said liquid to, through and/or around one of said two reagent dots does not substantially affect flow of said liquid sample to, through and/or around said other reagent dot, each of said two reagent dots is neither a reagent line across the entire width of said matrix in a direction perpendicular to the direction of said liquid flow nor a complete circle of a reagent line circulating the center or sample or liquid application site of said test device, and after a liquid flows laterally along said test device and passes said at least two reagent dots, detectable signals are formed at said at least two reagent dots to provide for flow control information, and:
1) to function as an internal control; or
2) to provide for internal calibration information for said test device; or
3) to function as an internal control and to provide for internal calibration information for said test device, and wherein
said internal calibration information is for quantification of an analyte,
said flow control information allows internal calibration within said test device for perturbation in test results caused by variability in flow rate or flow pattern laterally across the surface and/or along the length of a flow field, and
at least a quarter, a third, half of or all said reagent dots have a diameter of about 0.1-1 µm, 1-10 µm, 10-50 µm, 51-100 µm, 101-200 µm, 201-300 µm, or 301-400 µm.

2. The test device of claim 1, which test device further comprises a detection site to indicate presence, absence and/or amount of an analyte in a liquid sample.

3. The test device of claim 1, wherein the at least two reagent dots form a line that is substantially parallel to the liquid flow direction, a line that is substantially perpendicular to the liquid flow direction and/or a line that is at a predetermined angle relative to the liquid flow direction.

4. The test device of claim 1, wherein the detectable signal is formed at one or more of the at least two reagent dots to function as an internal control for the test device.

5. The test device of claim 4, wherein the detectable signal is formed at a single reagent dot to function as an internal control for the test device.

6. The test device of claim 4, wherein the detectable signals are formed at a plurality of reagent dots to function as an internal control for the test device.

7. The test device of claim 4, wherein the internal control is an internal control for cross reactivity or an interfering substance, an internal positive control, and/or an internal negative control.

8. The test device of claim 1, wherein the detectable signals are formed at the at least two reagent dots to provide internal calibration information for the test device.

9. The test device of claim 8, wherein the formation of the detectable signals at the at least two reagent dots is independent from the presence, absence and/or amount of the analyte in a liquid sample.

10. The test device of claim 8, wherein each of the at least two reagent dots comprises a reagent that binds to a labeled binding reagent for the analyte.

11. The test device of claim 8, wherein the detectable signals are formed at the at least two reagent dots to provide for internal calibration information for the desired analyte testing range.

12. The test device of claim 8, wherein the at least two reagent dots form a line that is substantially parallel to the liquid flow direction, a line that is substantially perpendicular to the liquid flow direction and/or a line that is at a predetermined angle relative to the liquid flow direction.

13. The test device of claim 8, wherein the test device does not comprise a detection site to indicate presence, absence and/or amount of an analyte in a liquid sample and the detectable signals are formed at the at least two reagent dots to provide for internal calibration information for the test device.

14. The test device of claim 1, wherein the test device does not comprise a detection site to indicate presence, absence and/or amount of an analyte in a liquid sample and the at least two reagent dots comprise a binding reagent that generates signals of specific signal strengths relative to one another or absolute signal strengths of differing levels.

15. The test device of claim 1, wherein the detectable signals are formed to provide for flow control information, to function as an internal control and to provide for internal calibration information for the test device.

16. The test device of claim 1, wherein a portion of the matrix, upstream from the at least two of the reagent dots, comprises a dried, labeled reagent, the labeled reagent being capable of being moved by a liquid or liquid sample to the at least two of the reagent dots and/or a test site to generate a detectable signal.

17. The test device of claim 1, wherein the distance between edges of at least two of the reagent dots is about 1-10 µm, 10-50 µm, 51-100 µm, 101-200 µm, 201-300 µm, or 301-400, µm.

18. A method for providing for flow control information, internal control or internal calibration information for a test device, which method comprises:

a) contacting a liquid with the test device of claim 1, wherein the liquid is applied to a site of said test device upstream of said at least two reagent dots;
b) transporting a labeled reagent to said at least two reagent dots; and
c) assessing the presence, absence, amount and/or pattern of signal(s) generated by said labeled reagent at said at least two reagent dots to provide for flow control information, and:
 1) to function as an internal control or;
 2) to provide for internal calibration information for said test device; or
 3) to function as an internal control and to provide for internal calibration information for said test device, and
wherein
said internal calibration information is for quantification of an analyte,
said flow control information allows internal calibration within said test device for perturbation in test results caused by variability in flow rate or flow pattern laterally across the surface and/or along the length of a flow field, and
at least a quarter, a third, half of or all said reagent dots have a diameter of about 0.1-1 µm, 1-10 µm, 10-50 µm, 51-100 µm, 101-200 µm, 201-300 µm, or 301-400 µm.

19. The method of claim 18, wherein the liquid and the labeled reagent are premixed to form a mixture and the mixture is applied to the test device.

20. The method of claim 18, wherein the test device comprises a dried labeled reagent before use and the dried labeled reagent is solubilized or resuspended, and transported to the at least two reagent dots by the liquid.

21. The method of claim 18, wherein the detectable signals are formed at the at least two reagent dots to:
a) to provide for flow control information;
b) to function as an internal control; and
c) to provide for internal calibration information for the test device.

22. The method of claim 18, which further comprises detecting an analyte in a liquid sample.

* * * * *